United States Patent
Kawaura et al.

(10) Patent No.: US 10,231,731 B2
(45) Date of Patent: Mar. 19, 2019

(54) PUNCTURE NEEDLE ASSEMBLY

(71) Applicant: TERUMO KABUSHIKI KAISHA, Shibuya-ku (JP)

(72) Inventors: Masakatsu Kawaura, Kanagawa (JP); Nao Yokoi, Kanagawa (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 311 days.

(21) Appl. No.: 14/867,332

(22) Filed: Sep. 28, 2015

(65) Prior Publication Data

US 2016/0015386 A1    Jan. 21, 2016

Related U.S. Application Data

(63) Continuation of application No. PCT/JP2013/059887, filed on Apr. 1, 2013.

(51) Int. Cl.
*A61B 17/34* (2006.01)
*A61B 17/06* (2006.01)
(Continued)

(52) U.S. Cl.
CPC .... *A61B 17/06109* (2013.01); *A61B 17/3403* (2013.01); *A61B 17/0485* (2013.01);
(Continued)

(58) Field of Classification Search
CPC .............. A61B 17/06; A61B 17/06066; A61B 17/06109; A61B 17/062; A61B 17/0625;
(Continued)

(56) References Cited

U.S. PATENT DOCUMENTS 6,641,525 B2 * 11/2003 Rocheleau ......... A61B 17/0401
600/30
6,908,425 B2 * 6/2005 Luscombe ......... A61B 1/00087
600/30

(Continued)

FOREIGN PATENT DOCUMENTS

| JP | 2005-518899 A | 6/2005 |
| JP | 2010-12281 A | 1/2010 |
| JP | 2010-99499 A | 5/2010 |

OTHER PUBLICATIONS

International Search Report (PCT/ISA/210) dated May 28, 2013, by the Japanese Patent Office as the International Searching Authority for International Application No. PCT/JP2013/059887.

*Primary Examiner* — Ryan J Severson
(74) *Attorney, Agent, or Firm* — Buchanan Ingersoll & Rooney PC

(57) ABSTRACT

A puncture needle assembly is disclosed, which includes a puncture needle adapted to puncture biological tissue; and a connector adapted to connect an elongated body insertable in a living body to a needle tip section of the puncture needle, the connector having a dissecting section adapted to dissect biological tissue by moving in a direction opposite to a direction in which the puncture needle punctures the biological tissue. The puncture needle assembly further includes a connection mechanism capable of connecting the puncture needle and the connector to each other; and a rotation restricting mechanism adapted to restrict rotation about an axis of the connector in relation to the puncture needle.

20 Claims, 22 Drawing Sheets

(51) Int. Cl.
    *A61B 17/04*     (2006.01)
    *A61B 17/00*     (2006.01)
    *A61F 2/00*      (2006.01)

(52) U.S. Cl.
    CPC . *A61B 17/3468* (2013.01); *A61B 2017/00477* (2013.01); *A61B 2017/00805* (2013.01); *A61B 2017/0608* (2013.01); *A61B 2017/06042* (2013.01); *A61B 2017/3407* (2013.01); *A61F 2/0036* (2013.01)

(58) Field of Classification Search
    CPC . A61B 17/34; A61B 17/3403; A61B 17/3415; A61B 17/3417; A61B 17/3468; A61B 2017/00477; A61B 2017/00486; A61B 2017/00805; A61B 2017/0608; A61B 2017/061; A61B 2017/06104; A61B 2017/320044; A61B 2017/320056; A61B 2017/3454; A61B 2017/3458; A61F 2/0031; A61F 2/0036; A61F 2/0045
    See application file for complete search history.

(56) References Cited

U.S. PATENT DOCUMENTS

| | | | | |
|---|---|---|---|---|
| 6,911,003 B2* | 6/2005 | Anderson | ......... | A61B 17/0401 |
| | | | | 600/30 |
| 7,070,556 B2* | 7/2006 | Anderson | ......... | A61B 17/0401 |
| | | | | 112/169 |
| 7,112,171 B2* | 9/2006 | Rocheleau | ........ | A61B 17/0401 |
| | | | | 600/37 |
| 7,131,943 B2* | 11/2006 | Kammerer | ........ | A61B 17/0469 |
| | | | | 600/30 |
| 7,364,541 B2* | 4/2008 | Chu | ................ | A61B 17/00234 |
| | | | | 600/30 |
| 7,371,245 B2* | 5/2008 | Evans | ............. | A61B 17/06066 |
| | | | | 606/151 |
| 8,911,464 B2* | 12/2014 | Kawaura | ........... | A61B 17/3468 |
| | | | | 606/185 |
| 8,979,732 B2* | 3/2015 | Montpetit | ....... | A61B 17/06109 |
| | | | | 600/30 |
| 9,011,475 B1* | 4/2015 | Yokoi | ............... | A61B 17/3468 |
| | | | | 606/185 |
| 9,017,357 B1* | 4/2015 | Kawaura | ............... | A61B 17/42 |
| | | | | 606/185 |
| 9,439,676 B2* | 9/2016 | Kawaura | ........... | A61B 17/3468 |
| 2002/0077526 A1* | 6/2002 | Kammerer | ........ | A61B 1/00087 |
| | | | | 600/30 |
| 2003/0171644 A1 | 9/2003 | Anderson et al. | | |
| 2003/0176762 A1* | 9/2003 | Kammerer | ........ | A61B 17/0469 |
| | | | | 600/30 |
| 2003/0176875 A1* | 9/2003 | Anderson | ......... | A61B 17/0401 |
| | | | | 606/151 |
| 2004/0087970 A1 | 5/2004 | Chu et al. | | |
| 2005/0143618 A1* | 6/2005 | Anderson | ......... | A61B 17/0401 |
| | | | | 600/29 |
| 2006/0015069 A1 | 1/2006 | Evans et al. | | |
| 2008/0234543 A1 | 9/2008 | Goldwasser | | |
| 2011/0144418 A1 | 6/2011 | Ogdahl et al. | | |
| 2012/0065462 A1 | 3/2012 | Montpetit et al. | | |
| 2013/0253531 A1* | 9/2013 | Kawaura | ............ | A61B 17/3468 |
| | | | | 606/119 |
| 2015/0011820 A1* | 1/2015 | Kawaura | ............ | A61B 17/0482 |
| | | | | 600/30 |
| 2015/0065791 A1* | 3/2015 | Kawaura | ............ | A61B 17/3468 |
| | | | | 600/37 |
| 2015/0073206 A1* | 3/2015 | Kawaura | ............ | A61B 17/0469 |
| | | | | 600/30 |
| 2015/0073465 A1* | 3/2015 | Ariura | .................. | A61B 5/6885 |
| | | | | 606/185 |
| 2015/0080644 A1* | 3/2015 | Kawaura | ................ | A61F 2/0045 |
| | | | | 600/30 |
| 2015/0133789 A1* | 5/2015 | Ariura | ................ | A61B 17/0482 |
| | | | | 600/461 |
| 2015/0164549 A1* | 6/2015 | Kawaura | ........... | A61B 17/0469 |
| | | | | 600/30 |
| 2015/0164627 A1* | 6/2015 | Kawaura | ........... | A61B 17/0482 |
| | | | | 600/30 |
| 2016/0015386 A1* | 1/2016 | Kawaura | .......... | A61B 17/06109 |
| | | | | 606/185 |
| 2016/0015414 A1* | 1/2016 | Kawaura | ................ | A61F 2/0045 |
| | | | | 606/170 |
| 2016/0015501 A1* | 1/2016 | Kawaura | ............ | A61B 17/0482 |
| | | | | 600/30 |
| 2016/0022262 A1* | 1/2016 | Kawaura | ............ | A61B 17/0482 |
| | | | | 600/30 |

* cited by examiner

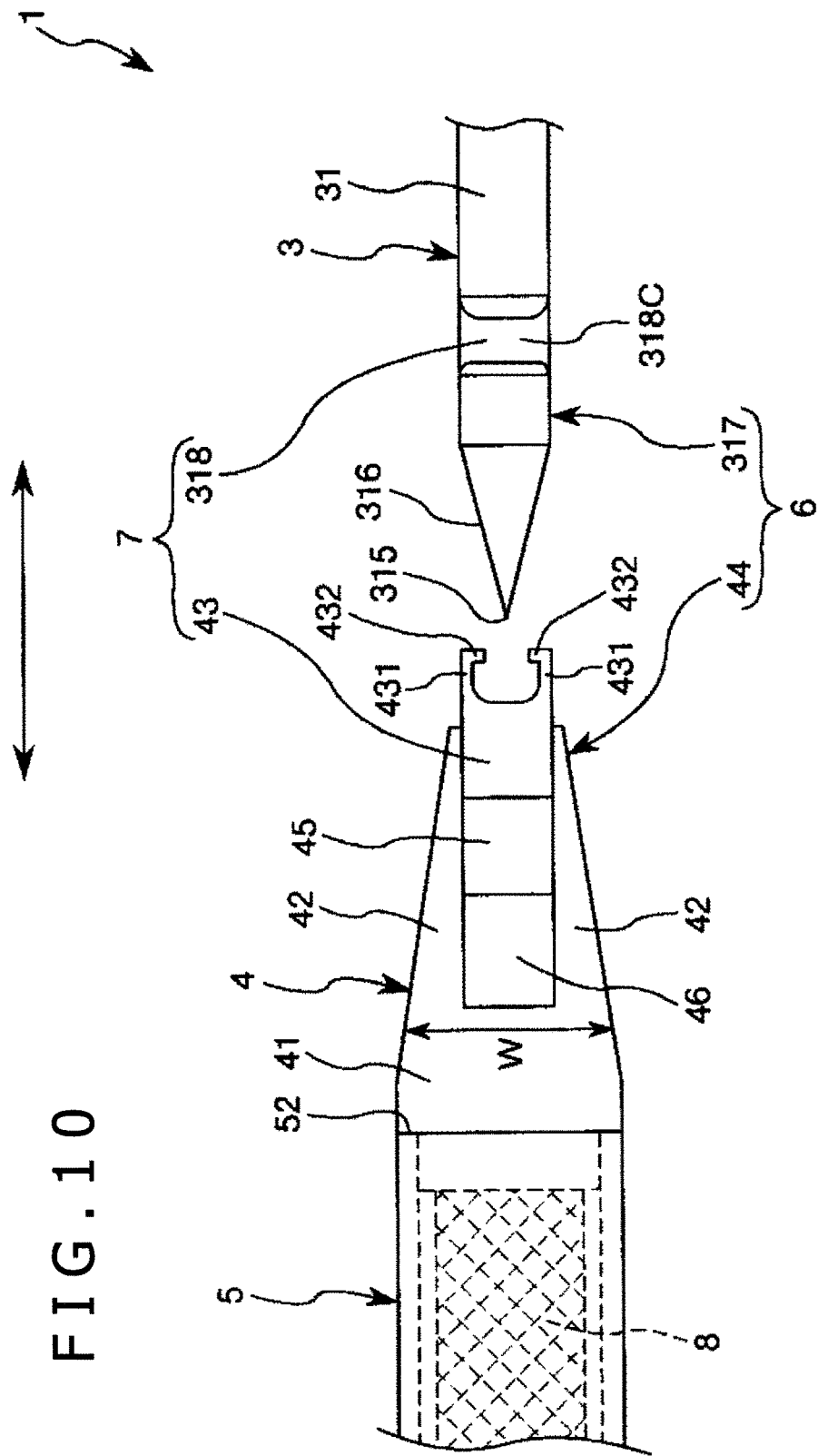

PUNCTURE NEEDLE ASSEMBLY

CROSS-REFERENCES TO RELATED APPLICATIONS

This application is a continuation of International Application No. PCT/JP2013/059887 filed on Apr. 1, 2013, the entire content of which is incorporated herein by reference.

TECHNICAL FIELD

The present disclosure relates to a puncture needle assembly.

BACKGROUND DISCUSSION

If a person suffers from a urinary incontinence, for example, if a person suffers from a stress urinary incontinence, then urine leakage can be caused by application of abdominal pressure during normal exercise or by laughing, coughing, sneezing or the like. The cause of this may be, for example, that the pelvic floor muscle which is a muscle for supporting the urethra is loosened by birth or the like.

For the treatment of urinary incontinence, a surgical treatment is effective, in which there is used, for example, a tape-shaped (elongated) implant called "sling." The sling is indwelled inside the body and the urethra is supported by the sling (see, for example, Japanese Patent Laid-open No. 2010-99499). In order to indwell the sling inside the body, an operator would incise the vagina with a surgical knife, dissect the biological tissue between the urethra and the vagina, and make the dissected region and the outside communicate with each other using a puncture needle via an obturator foramen of a pelvis, forming a puncture hole. Then, by use of such a puncture hole, the sling is indwelled into the body.

If the vagina is incised once, however, a situation may occur that the sling is exposed to the inside of the vagina from a wound caused by the incision of the vagina, and complications may be caused by an infection from the wound or the like. Further, since the vagina is incised, there can be such a defect that the invasion is relatively great and the burden on the patient is relatively heavy. Further, the urethra may be damaged by a surgical knife in the course of the procedure by the operator. In addition, the fingertip of the operator may be damaged or injured by a surgical knife.

In addition, for example, for indwelling the sling in a predetermined orientation, the biological tissue must be dissected in a width much greater than the width of the sling, which can lead to a relatively heavy burden on the patient.

SUMMARY

A puncture needle assembly is disclosed, which can help ensure that at the time of inserting into a patient's body an elongated body in a predetermined orientation, the inserting operation can be carried out relatively easily and reliably, the burden on the patient is little, the safety of the patient is high, and the safety of the operator is also high.

In accordance with an exemplary embodiment, a puncture needle assembly is disclosed, which can include a puncture needle adapted to puncture biological tissue and a connector adapted to connect an elongated body insertable in a living body to a needle tip section of the puncture needle, the connector having a dissecting section adapted to dissect biological tissue by moving in a direction opposite to a direction in which the puncture needle punctures the biological tissue, wherein the puncture needle assembly can further includes a connection mechanism capable of connecting the puncture needle and the connector to each other and a rotation restricting mechanism adapted to restrict rotation about an axis of the connector in relation to the puncture needle.

In the puncture needle assembly, preferably, the connection mechanism is provided in the puncture needle and the connector, and is so configured as to connect the puncture needle and the connector in such a manner that a positional relation of the puncture needle and the connector in a direction of rotation about the axis is constant.

In the puncture needle assembly, the connection mechanism may be so configured as to connect the puncture needle and the connector by relatively moving the puncture needle and the connector in an axial direction.

The puncture needle assembly may be so configured that the connection mechanism can include a first connection section provided in the puncture needle, and a second connection section provided in the connector. The first connection section can have a first recess in a needle tip section of the puncture needle and the second connection section has a connector-side engaging section, which engages with the first recess in a connected state.

In the puncture needle assembly, preferably, for example, the connector-side engaging section can have a connector-side projection, which projects toward a proximal side in the axial direction.

In the puncture needle assembly, preferably, for example, one of the first connection section and the second connection section has a second recess and the other of the first connection section and the second connection section has a projection which engages with the second recess in the connected state.

In the puncture needle assembly, an inside of the first recess may be formed to range to a more distal side than an entrance to the first recess.

In the puncture needle assembly, the inside of the first recess may be formed to range to a more proximal side than the entrance to the first recess.

In the puncture needle assembly, preferably, for example, the connector is provided, on a distal side of the connector-side engaging section of the connector, with a hole into which a needle tip section of the puncture needle is inserted at a time of connecting the puncture needle and the connector.

The puncture needle assembly may be so configured that the second connection section has a tubular section into which a needle tip section of the puncture needle is inserted and the needle tip section of the puncture needle is inserted into the tubular section at a time of connecting the puncture needle and the connector.

In the puncture needle assembly, the connector-side engaging section may have a connector-side projecting piece which is elastic and projects toward a distal side in the axial direction.

In the puncture needle assembly, preferably, for example, the connection mechanism can be configured to connect the puncture needle and the connector by relatively rotating at least part of the puncture needle and at least part of the connector.

The puncture needle assembly may be so configured that the rotation restricting mechanism can include a first rotation restricting section provided in the puncture needle, and a second rotation restricting section provided in the connector. The first rotation restricting section can have a first recess in a needle tip section of the puncture needle and the second rotation restricting section can have a contact surface, which makes contact with an inner surface of the first recess in a connected state.

The puncture needle assembly may be so configured that the rotation restricting mechanism can include a first rotation restricting section provided in the puncture needle, and a second rotation restricting section provided in the connector. The first rotation restricting section can have a puncture needle-side projecting piece which is elastic and projects toward a proximal side in an axial direction and the second rotation restricting section has a connector-side projecting piece which is elastic, projects toward a distal side in an axial direction and makes contact with the puncture needle-side projecting piece in a connected state.

The puncture needle assembly may further include a connection release preventing mechanism adapted to help prevent a connected state from being released.

When the puncture needle assembly disclosed herein is used for inserting into a patient's body an elongated boy in a predetermined orientation, the inserting operation can be performed relatively easily and assuredly, with relatively little burden on the patient and while helping ensure high safety of both the patient and the operator.

For instance, when the puncture needle assembly disclosed herein is used for treatment of female urinary incontinence, an elongated implant for treatment of urinary incontinence can be embedded by a low invasive procedure, without need to incise the vagina. In addition, it is possible to avoid the risk that, as in the case of incision of the vagina, the implant is exposed to the inside of the vagina through a wound caused by the incision or a complication, such as an infection from the wound can occur. Thus, the implant can be embedded reliably and in very high safety.

For example, since biological tissue can be dissected in a predetermined width by the dissecting section, the implant can be embedded relatively assuredly by a very low invasive manual procedure.

In addition, since the rotation of the connector (dissecting section) about an axis in relation to the puncture needle in the connected state of the puncture needle and the connector is restricted, the implant can be embedded to be oriented in the intended orientation.

In accordance with an exemplary embodiment, since the operator need not perform incision or the like, injuring the fingertip with a surgical knife or the like can be prevented from occurring, so that safety can be relatively ensured.

A puncture needle assembly is disclosed, comprising: a puncture needle adapted to puncture biological tissue; a connector adapted to connect an elongated body insertable in a living body to a needle tip section of the puncture needle, the connector having a dissecting section adapted to dissect biological tissue by moving in a direction opposite to a direction in which the puncture needle punctures the biological tissue; a connection mechanism capable of connecting the puncture needle and the connector to each other; and a rotation restricting mechanism adapted to restrict rotation about an axis of the connector in relation to the puncture needle.

A puncture needle assembly is disclosed comprising: a puncture needle adapted to puncture biological tissue; a connector adapted to connect an elongated body insertable in a living body to a needle tip section of the puncture needle, the connector having a dissecting section adapted to dissect biological tissue by moving in a direction opposite to a direction in which the puncture needle punctures the biological tissue; and a connection mechanism capable of connecting the puncture needle and the connector to each other.

A method is disclosed of inserting an elongated body in a living body, the method comprising: puncturing biological tissue with a puncture needle; connecting the elongated body to a needle tip section of the puncture needle; connecting a connector to the puncture needle, the connector having a dissecting section adapted to dissect the biological tissue by moving in a direction opposite to a direction in which the puncture needle punctures the biological tissue; and moving the connector in the direction opposite to the direction in which the puncture needle punctures the biological tissue

BRIEF DESCRIPTION OF THE DRAWINGS

FIG. 10 is a plan view showing the puncture needle assembly according to the first embodiment of the present disclosure;

DETAILED DESCRIPTION

A puncture needle assembly according to exemplary embodiments of the present disclosure will be described in detail below, referring to non-limitative preferred embodiments illustrated in the attached drawings.

Figures 11A, 11B:
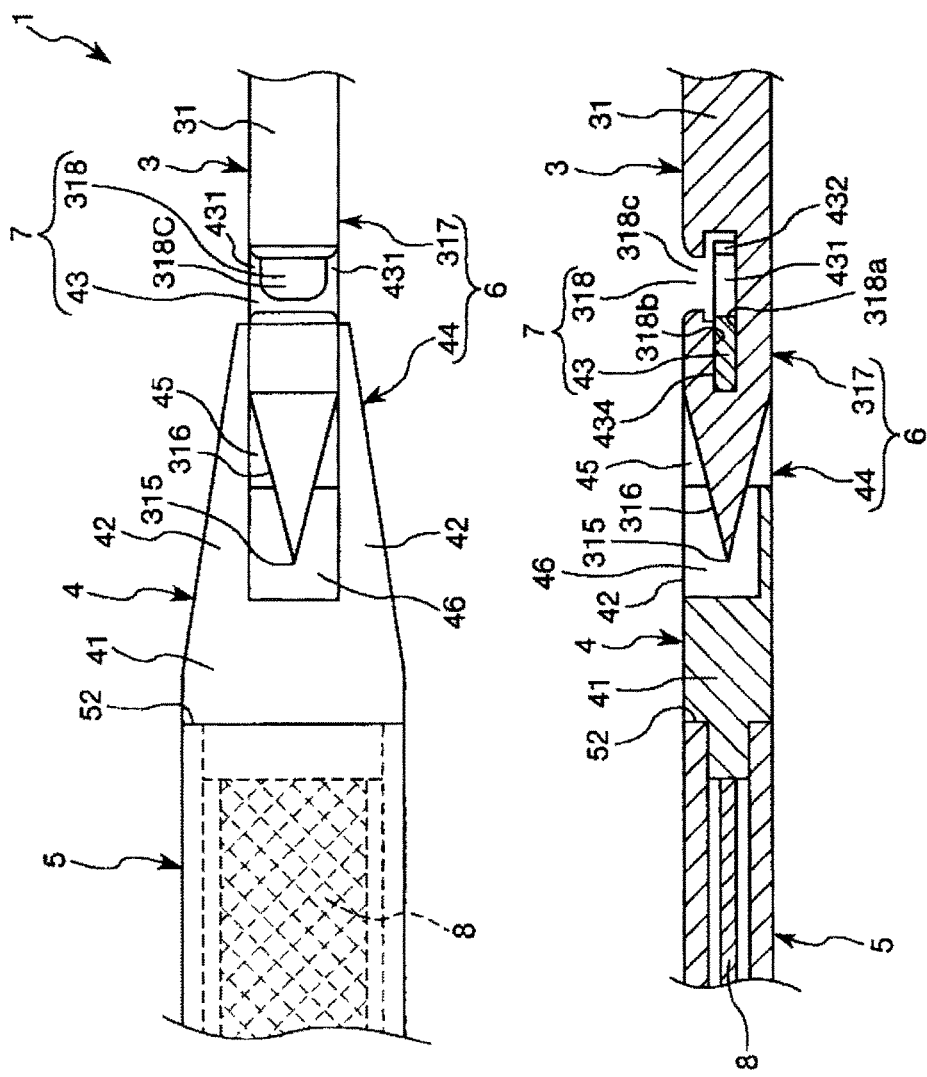
FIGS. 11A and 11B illustrate a connected state in which a puncture needle and a connector of the puncture needle assembly shown in FIG. 10 are connected to each other.
Figure 12A:
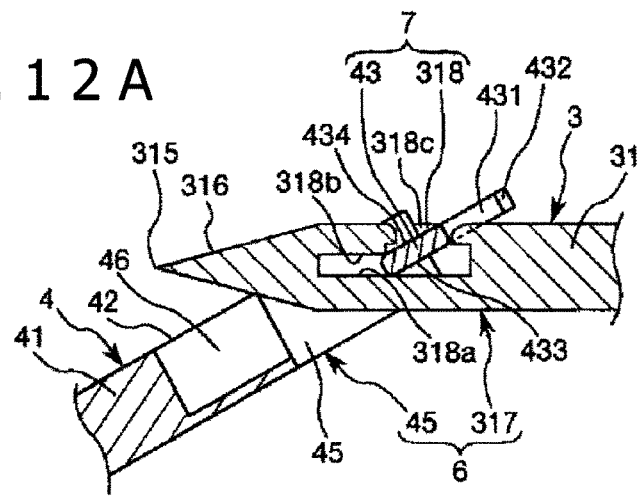
FIGS. 12A to 12C are sectional views illustrating a procedure for connecting the puncture needle and the connector of the puncture needle assembly shown in FIG. 10.
Figure 12B:
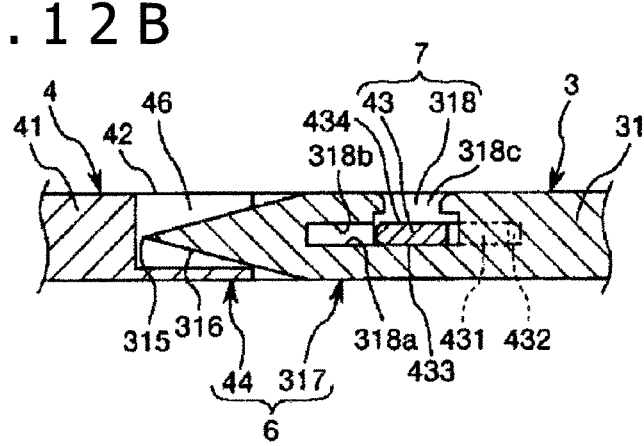
Figure 12C:
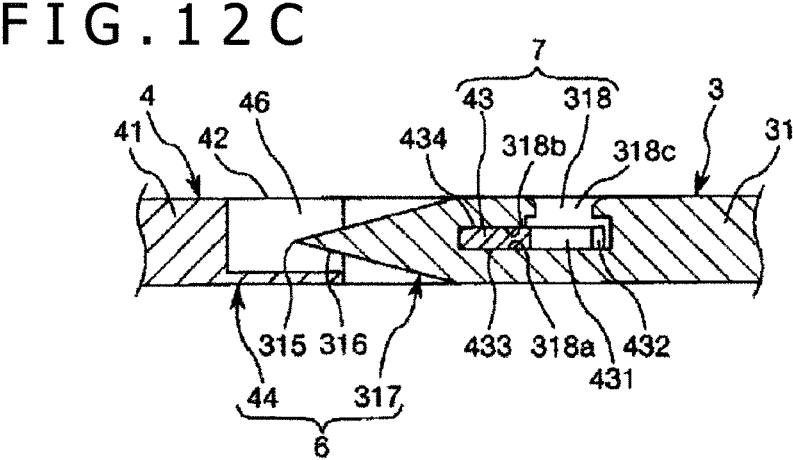

FIGS. 1 to 8 are sectional views for sequentially showing a method of using a puncture needle assembly according to a first embodiment of the present disclosure. FIG. 9 is a side view as viewed in the direction of arrow A in FIG. 1. FIG. 10 is a plan view showing the puncture needle assembly according to the first embodiment of the present disclosure. FIGS. 11A and 11B illustrate a connected state in which a puncture needle and a connector of the puncture needle assembly shown in FIG. 10 are connected, wherein FIG. 11A is a plan view and FIG. 11B is a sectional view. FIGS. 12A to 12C are sectional views illustrating a procedure for connecting the puncture needle and the connector of the puncture needle assembly shown in FIG. 10.

In the following description, for convenience of explanation, the upper side in FIGS. 1 to 9 will be referred to as "upper" or "upper side," and the lower side in the figures as "lower" or "lower side." In addition, the side of a needle tip will be referred to as "distal" side, and the opposite side as "proximal" side.

In addition, a puncture needle 31 and a connector assembly 2 can be curved (bent) respectively, as will be described later, but they are depicted in a substantially straight form in FIGS. 10 to 12C (the same applies to the figures illustrating the other embodiments).

FIGS. 1 to 4 and FIGS. 9 to 11B illustrate a medical device set 10A, which has a puncture needle assembly 1. The medical device set 10A can include a puncture apparatus 10, the connector assembly 2, a connection mechanism 6 which is provided in the puncture needle 31 (described later) of the puncture apparatus 10 and a connector 4 (described later) of the connector assembly 2, and which can connect the puncture needle 31 and the connector 4 so that the positional relation of the puncture needle 31 and the connector 4 in the direction of rotation about an axis is constant; and a rotation restricting mechanism 7 which is provided in the puncture needle 31 and the connector 4, and which can restrict rotation about the axis of the puncture needle 31 in relation to the connector 4 in a connected state in which the puncture needle 31 and the connector 4 are connected by the connection mechanism 6 (this state will hereinafter referred also to as simply as "the connected state of the puncture needle 31 and the connector 4").

In accordance with an exemplary embodiment, the puncture needle assembly 1 can include the puncture needle 31 (puncture member 3) which punctures biological tissue 700, an implant (in-body indwelling instrument) 8 for treatment of urinary incontinence, which is an elongated body embeddable (insertable) in a living body, the connector 4 for connecting the implant 8 to a needle tip section of the puncture needle 31, a sheath (tube) (elongated body) 5 which is a tubular body accommodating the implant 8, serving as an elongated retaining member connected to the connector 4 and having a part for retaining the implant 8, the connection mechanism 6 provided in the puncture needle 31 and the connector 4, and the rotation restricting mechanism 7 provided in the puncture needle 31 and the connector 4. In accordance with an exemplary embodiment, the puncture needle assembly 1 (medical device set 10A) is a medical device for use in treatment of female urinary incontinence, for example, for use in embedding in a living body the implant 8 for treatment of urinary incontinence. The configuration of each component will be described below.

As shown in FIGS. 1 to 4 and 9, the puncture device 10 can include the puncture member 3, and a support member 20 by which the puncture member 3 can be turnably supported. Note that the puncture device 10 may further include a bar-shaped urethral-insertion member inserted into a urethra 100, and a bar-shaped vaginal-insertion member inserted into a vagina 200. In accordance with an exemplary embodiment, the urethral-insertion member and the vaginal-insertion member can each preferably be supported on and fixed to the support member 20.

The puncture member 3 can include a puncture needle 31 which punctures biological tissue 700, a shaft section 33, and a interlock section 32 interlocking the puncture needle 31 and the shaft section 33.

The puncture needle 31 has a sharp needle tip 315 at the distal end of the puncture needle 31, and curved in a circular arc shape, with the shaft section 33 as a center of the circle. The axis of the puncture needle 31 and the axis of the shaft section 33 are in a positional relationship of skew lines, which can help ensure that when the puncture member 3 is turned about the shaft section 33, the needle tip 315 of the puncture needle 31 moves in a plane orthogonal to the axis of the shaft section 33, for example, a plane to which the axis of the shaft section 33 is normal, along the circular arc. Note that the needle tip 315 may not necessarily be sharp but may be rounded, for example.

The center angle of the circular arc of the puncture needle 31 is not particularly limited, but may be appropriately set according to various conditions. In practice, however, the center angle is so set that when the biological tissue 700 is punctured by the puncture needle 31, a piercing hole (puncture hole) 500 having a circular arc shape (as described later) is formed in the biological tissue 700. Such a center angle can be, for example, preferably 150 to 270 degrees, more preferably 170 to 250 degrees, and further preferably 190 to 230 degrees.

While the needle tip 315 of the puncture needle 31 is oriented counterclockwise in FIGS. 1 to 4 in this embodiment, the needle tip 315 may be oriented clockwise in the figures.

The puncture needle 31 can be formed with a tapered section 316 where an outer diameter gradually increases towards a proximal end of the needle tip 315.

While the cross-sectional shape of the peripheral surface of the puncture needle 31 is circular in this embodiment, the cross-sectional shape is not limited to this, and may be non-circular. In addition, while the puncture needle 31 is a solid needle in this embodiment, the puncture needle 31 may be a hollow needle.

The puncture needle 31 as above has a connection section (first connection section) 317 at a needle tip section (distal portion) of the puncture needle 31. The connection section 317 has a recess (first recess) 318 formed on the proximal side of the tapered section 316. The recess 318 is open not only to the viewer's side of the sheet surface in FIG. 10, but also respectively to both sides with respect to the vertical direction in FIG. 10. In addition, the inside of the recess 318 is formed to range or extend to a more distal side than an entrance 318c to the recess 318 and range or extend to a more proximal side than the entrance 318c to the recess 318. In accordance with an exemplary embodiment, for example, the inside of the recess 318 is formed to be broader, to the distal side and to the proximal side, than the entrance 318c to the recess 318. A bottom surface 318a and a ceiling surface 318b of the recess 318 are each a plain surface. In addition, the recess 318 can function also as a first rotation restricting section.

The shaft section 33 serves as a rotating shaft of the puncture member 3 (puncture needle 31), and is turnably disposed on the support member 20.

As shown in FIG. 9, the shaft section 33 penetrates the support member 20 in the left-right direction in the figure. The shaft section 33 is formed, at a distal portion and a proximal portion thereof, with a flange 331 and a flange 332, between which is interposed the support member 20. The flanges 331, 332 can restrict axial movement of the shaft section 33 relative to the support member 20.

At an end portion, on the opposite side from the puncture needle 31, of the shaft section 33 is provided a grip section 34 as an operating section for turning the puncture member 3. The grip section 34 is rectangular parallelepiped in shape in this embodiment. At the time of turning the puncture member 3, the grip section 34 can be gripped with fingers and is turned in a predetermined direction. Note that the shape of the grip section 34 is naturally not limited to the illustrated.

The interlock section 32 is a part for interlock the proximal end of the puncture needle 31 and the shaft section 33.

The material constituting the puncture member 3 is not specifically restricted. Examples of the material applicable here include various metallic materials such as stainless steel, aluminum or aluminum alloys, titanium or titanium alloys, etc. and various resin materials such as polyethylene, polyimides, polyamides, polyester elastomers, polypropylene, etc.

The support member 20 is a member by which the puncture member 3 is turnably supported. Note that in FIGS. 1 to 4, the support member 20 is omitted from the drawings.

The support member 20 can restrict the position of the puncture member 3 so that the needle tip 315 of the puncture needle 31 passes between the urethra 100 and the vagina 200 when the puncture member 3 is turned to puncture the biological tissue 700. As a result, a piercing hole 500 in a circular arc shape is formed between the urethra 100 and the vagina 200 by the puncture needle 31.

The material constituting the support member 20 is not particularly limited. Examples of the material usable here include various resin materials such as polyethylene, polypropylene, polycarbonate, acrylonitrile-butadiene-styrene copolymer (ABS resin), etc.

As shown in FIGS. 10 to 12C, the connector assembly 2 can include an implant 8 for treatment of urinary incontinence that is embedded in a living body, the connector 4 for connecting the implant 8 indirectly to a needle tip section of the puncture needle 31, and a sheath 5.

The connector 4 has a connection section (second connection section) 44 which can include a main body section 41 and a projecting piece (connector-side engaging section) 43 as a connector-side projection projecting from the main body section 41 toward the proximal side in the axial direction.

The projecting piece 43 is plate-like in shape, and is so disposed as to be parallel to the sheet surface in FIG. 10. The projecting piece 43 is provided at a proximal portion of the projecting piece 43 with a pair of arm sections 431, which are disposed opposite to each other, project to the proximal side and are elastic. The arm sections 431 can be juxtaposed with each other along the vertical direction in FIG. 10. The arm sections 431 can be formed at their proximal portions with claws 432, which are disposed to face each other and project toward the inside.

In the connected state of the puncture needle 31 and the connector 4 shown in FIGS. 11A and 11B, the projecting piece 43 is in engagement with the recess 318 in the connection section 317 of the puncture needle 31. In accordance with an exemplary embodiment, for example, by the engagement of the projecting piece 43 and the recess 318, the puncture needle 31 and the connector 4 are connected so that the positional relation of the puncture needle 31 and the connector 4 in the direction of rotation about the axis is kept constant. In addition, the connected state can be reliably maintained. In accordance with an exemplary embodiment, for example, the claws 432 of the arm sections 431 of the projecting piece 43 are located inside the recess 318, and the claws 432 make contact with the proximal side (the right side in FIGS. 11A and 11B) of the ceiling surface 318b of the recess 318, whereby unintentional release of the connected state of the puncture needle 31 and the connector 4 can be securely prevented from occurring. As a result, the implant 8 can be embedded so that the implant 8 is oriented in the intended orientation. Note that the connection section 44 and the connection section 317 constitute a connection mechanism 6. As will be described later, the connection mechanism 6 is so configured as to interconnect the puncture needle 31 and the connector 4 by relatively moving the puncture needle 31 and the connector 4 in the axial direction. In addition, the claws 432 of the projecting piece 43 and the ceiling surface 318b of the recess 318 constitute a connection release preventing mechanism.

The projecting piece 43 can also function as a second rotation restricting section. In the connected state of the puncture needle 31 and the connector 4 depicted in FIGS. 11A and 11B, a lower surface (contact surface) 433 and an upper surface (contact surface) 434 of the projecting piece 43 make contact with inner surfaces of the recess 318 in the puncture needle 31, for example, with the bottom surface 318a and the ceiling surface 318b of the recess 318, whereby the connector 4 is inhibited (restrained) from rotating about the axis in relation to the puncture needle 31. As a result, the implant 8 can be embedded so that the implant 8 is oriented in the intended orientation. Note that the projecting piece (second rotation restricting section) 43 and the recess (first rotation restricting section) 318 constitute the rotation restricting mechanism 7.

The main body section 41 can have a tapered section where its width (the length in the vertical direction in FIG. 10) W gradually increases from the proximal side toward the distal side, and both side portions (both end portions with respect to the vertical direction in FIG. 10) of the main body section 41 constitute a dissecting section 42 which dissects the biological tissue 700 in a width approximately equal to the width of the implant 8. Note that the maximum value of the width W of the main body section 41 is set to be approximately equal to the width of the implant 8, which makes it possible to dissect the biological tissue 700 in a necessary and sufficient extent for embedding the implant 8 in the living body, and to form in the biological tissue 700 a piercing hole 500 having a necessary and sufficient width. Consequently, the implant 8 can be embedded relatively assuredly so that the implant 8 is oriented in the intended orientation, by a very low invasive procedure.

A hole 45 into which to insert a needle tip section of the puncture needle 31 at the time of connecting the puncture needle 31 and the connector 4 is formed in a proximal portion of the main body section 41, for example, in the main body section 41 on the distal side of the projecting piece 43. The hole 45 can be sized so that the needle tip section of the puncture needle 31 can be inserted in the hole 45, and the needle tip section of the puncture needle 31 penetrates the main body section 41 in the direction orthogonal to the sheet surface in FIG. 10.

The main body section 41 is formed, on the distal side of the hole 45, with a recess 46 communicating with the hole 45. The recess 46 is opening to the viewer's side of the sheet surface in FIG. 10. In accordance with an exemplary embodiment, due to the presence of the recess 46, interference between the needle tip section of the puncture needle 31 and the main body section 41 can be prevented from occurring at the time of connecting the puncture needle 31 and the connector 4.

The main body section 41 is flat-shaped in cross section, which can help ensure a reduced invasion and a lightened burden on the patient at the time of dissecting the biological tissue 700 by the dissecting section 42. Note that the cross-sectional shape of the main body section 41 is naturally not limited to a flat shape.

The material constituting the connector 4 is not particularly limited. Examples of the material applicable here include various resin materials such as polyethylene, polypropylene, polycarbonate, acrylonitrile-butadiene-styrene copolymer (ABS resin), etc.

A proximal portion of the sheath 5 is connected to a distal portion of the connector 4.

As shown in FIGS. 3 to 5 and 10, the sheath 5 is a tube (tubular body) which includes a distal opening 51 opening at the distal end of the sheath 5, and a proximal opening 52 opening at the proximal end of the sheath 5. The sheath 5 is curved in a circular arc shape.

The sheath 5 is formed therein with a lumen 55, which opens at the distal opening 51 and the proximal opening 52. The implant 8 can be inserted into the lumen 55. Note that while only one lumen is formed in this embodiment, the number of the lumen(s) is not limited to one; for example, two or more lumens may be formed.

The sheath 5 may be rigid, or may be soft. In accordance with an exemplary embodiment, for example, the sheath 5 may be flexible. In this embodiment, the sheath 5 is rigid. Here, "rigid" means that the sheath 5 has such a degree of rigidity that the sheath 5 by itself can maintain a circular arc-shaped curved state. The degree of curving (curvature) of the sheath 5 is preferably comparable to or smaller than the degree of curving of the puncture needle 31.

Such a configuration as above can help ensure that at the time of inserting the sheath 5 into the piercing hole 500 formed by the puncture needle 31 and the dissecting section 42 of the connector 4, the sheath 5 is prevented from being crushed (pressed down) in the piercing hole 500, and the sheath 5 can easily follow (be formed along) the curved shape of the piercing hole 500. As a result, the operation of inserting the sheath 5 together with the implant 8 into the piercing hole 500 (the living body) can be carried out relatively easily and reliably. In addition, by drawing the sheath 5 out of the piercing hole 500 (as described later) after the inserting operation, the implant 8 can be indwelled in the piercing hole 500 relatively easily and assuredly (see FIG. 6).

As shown in FIGS. 11A and 11B, the sheath 5 is flat-shaped, for example, elliptic in cross section, which can help ensure that at the time of preliminarily inserting the tape-like implant 8 in the lumen 55, the inserting operation can be carried out relatively easily. In addition, there can be an advantage that the piercing hole 500 can be provided with a space in which the implant 8 can be inserted in a relatively assured manner, and the orientation of the implant 8 can be restricted.

Note that the cross-sectional shape of the sheath 5 is not limited to a flat shape, but may be, for example, a circle.

The thickness direction (minor diameter direction) of the flat shape of the sheath 5 is oriented toward the side of the center of curvature of the sheath 5. This configuration can contribute to easier insertion of the sheath 5 into the piercing hole 500, as compared with the case where the width direction (major diameter direction) of the flat shape is oriented toward the side of the center of curvature of the sheath 5.

In accordance with an exemplary embodiment, the thickness direction of the flat shape of the sheath 5 agrees with the thickness direction of the flat shape of the main body section 41 of the connector 4, and the width direction of the flat shape of the sheath 5 coincides with the width direction of the flat shape of the main body section 41 of the connector 4.

Figure 4:
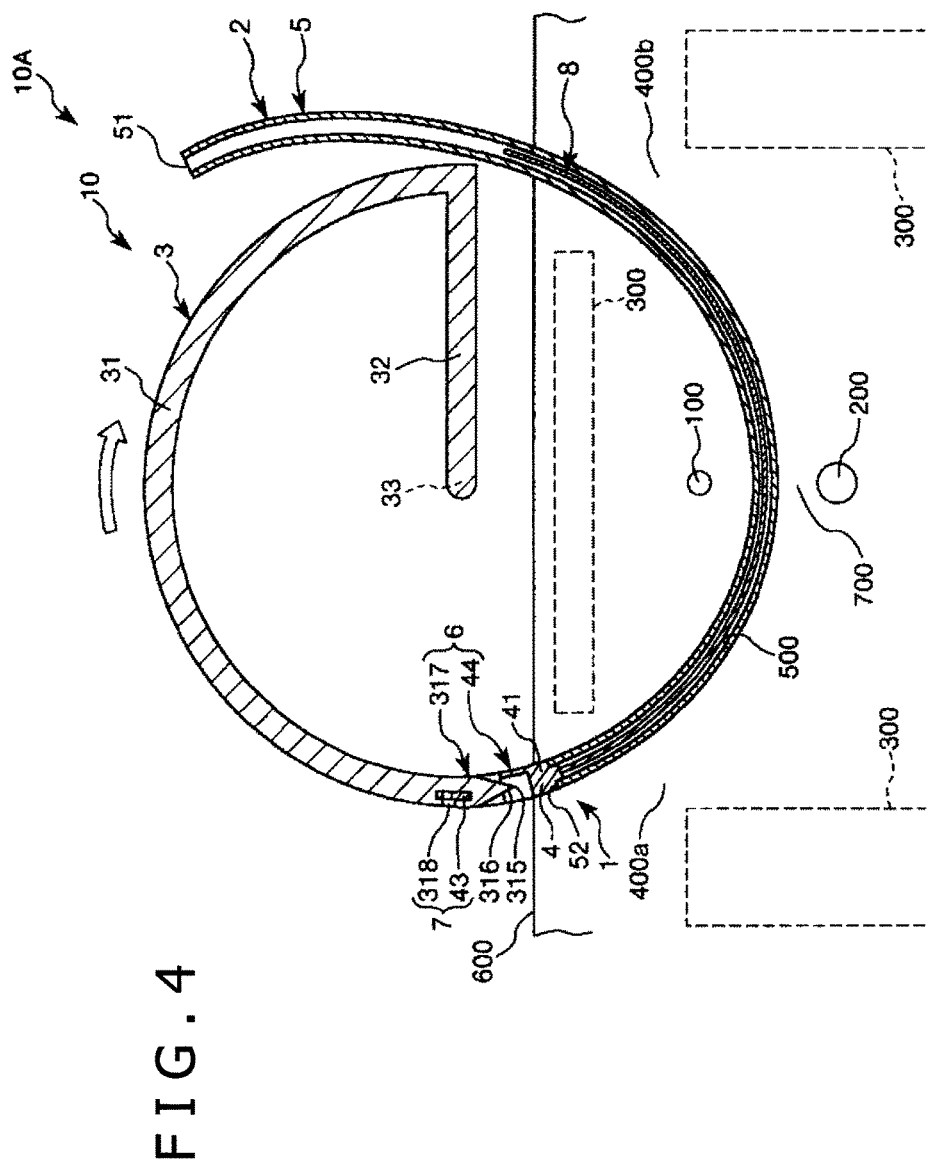
FIG. 4 is a sectional view for sequentially illustrating the method of using the puncture needle assembly according to the first embodiment.
Figure 5:
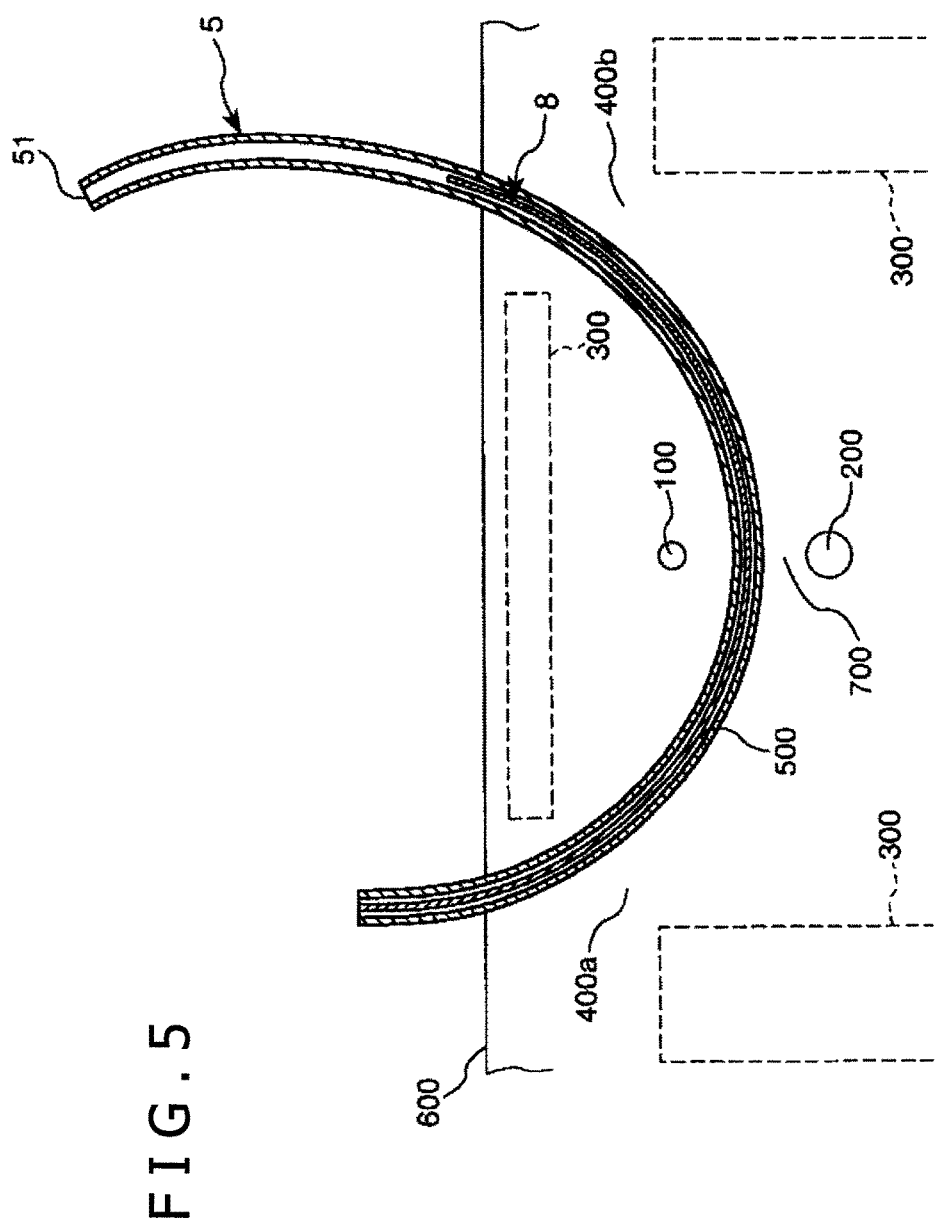
FIG. 5 is a sectional view for sequentially illustrating the method of using the puncture needle assembly according to the first embodiment.

The sheath 5, for example, preferably has an overall length greater than the overall length of the puncture needle 31, which can help ensure that the sheath 5 is longer than the overall length of the piercing hole 500 formed by the puncture needle 31, so that both end portions of the sheath 5 protrude from the piercing hole 500 in the state where the sheath 5 is inserted and passed in the piercing hole 500, as shown in FIGS. 4 and 5. At the time of pulling the sheath 5 out of the piercing hole 500, any of the protruding portions of the sheath 5 can be gripped to perform the pulling-out operation.

The material constituting the sheath 5 is not specifically restricted. Examples of the material applicable here include polyolefins such as polyethylene, polypropylene, ethylene-vinyl acetate copolymer, etc., modified polyolefins, polyamides (for example, nylon 6, nylon 46, nylon 66, nylon 610, nylon 612, nylon 11, nylon 12, nylon 6-12, nylon 6-66), thermoplastic polyimides, liquid crystal polymers such as aromatic polyesters, etc., polyphenylene oxide, polyphenylene sulfide, polycarbonate, polymethyl methacrylate, polyether, polyether-ether ketone, polyether imides, polyacetal, various thermoplastic elastomers based on styrene, polyolefin, polyvinyl chloride, polyurethane, polyester, polyamide, polybutadiene, trans-polyisoprene, fluoro-rubber, chlorinated polyethylene or the like, and copolymers, blends, polymer alloys and the like containing these polymers as main constituents, and these materials may be used either singly or as a mixture of two or more of them.

The implant 8 is an instrument, which is generally, called "sling" and which can be embedded for treatment of female urinary incontinence. For example, the implant 8 is an instrument for supporting the urethra 100, for example, for supporting the urethra 100 so as to restrict its movement away from the vagina 200 when the urethra 100 is about to move toward the vagina 200 side (see FIG. 8). The implant 8 is composed of a member, which is flexible and tape-like (elongated) in shape (see FIGS. 3 to 8). The implant 8 is accommodated in the sheath 5. The implant 8 may be connected to or not connected to the connector 4. Note that in this embodiment a proximal portion of the implant 8 is connected to a distal portion of the connector 4.

In this embodiment, the implant 8 is in a network form. The implant 8 may be composed, for example, of a network (lattice) form matter knitted by intersecting linear elements, or a network form braiding. The linear element may be one that is circular in cross section, or one that is flat-shaped in cross section, namely, that is tape-like (ribbon-like) in shape.

Note that the implant 8 naturally is not limited to network form ones.

The material constituting the implant 8 is not particularly limited. Example of the material usable here include various resin materials, fibers and the like which are biocompatible, such as polypropylene.

Figure 3:
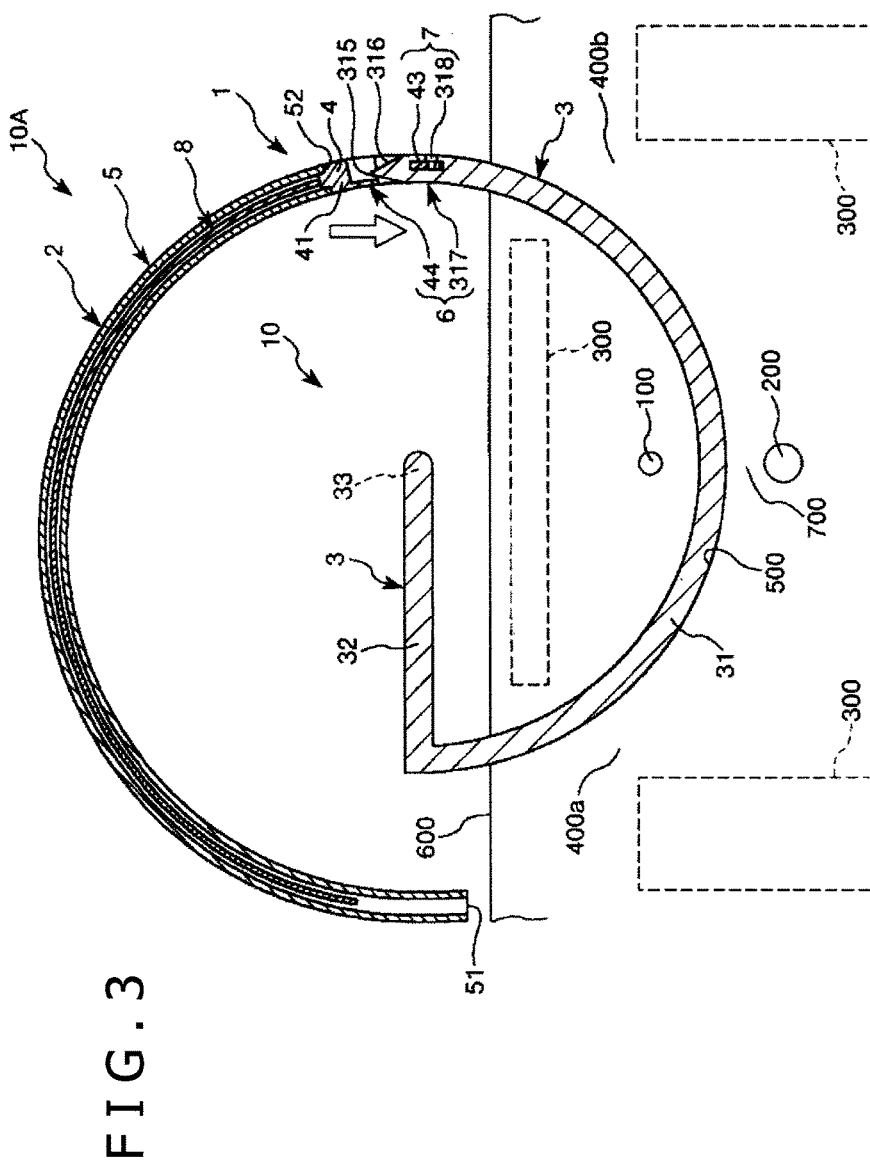
FIG. 3 is a sectional view for sequentially illustrating the method of using the puncture needle assembly according to the first embodiment.

The implant 8 may be preliminarily inserted (accommodated) in the sheath 5 as shown in FIG. 3, or may be inserted into the sheath 5 in the course of a procedure. Where the implant 8 is preliminarily inserted in the sheath 5, the procedure can be carried out relatively swiftly. Where the implant 8 is inserted into the sheath 5 in the course of a procedure, an implant 8 suitable for each individual case can be selected each time of the procedure. Note that in this embodiment, description will be made representatively of a case where the implant 8 is preliminarily inserted in the sheath 5.

As illustrated in FIGS. 3 and 4, in the connected state of the puncture needle 31 and the connector 4, the puncture member 3 is turned clockwise in the figures, the sheath 5 can be pulled together with the implant 8, while puncturing the biological tissue 700 by the puncture needle 31 and while further dissecting that part of the biological tissue 700 which has been punctured by the puncture needle 31 by the dissecting section 42 of the connector 4. As a result, the sheath 5 can be relatively easily inserted in and passed through the piercing hole 500 together with the implant 8, so that the subsequent indwelling of the implant 8 in the piercing hole 500 can be carried out relatively easily.

In accordance with an exemplary embodiment, an exemplary example of the method of using the medical device set 10A will be described below, referring to FIGS. 1 to 8 and FIGS. 12A to 12C.

Figure 1:
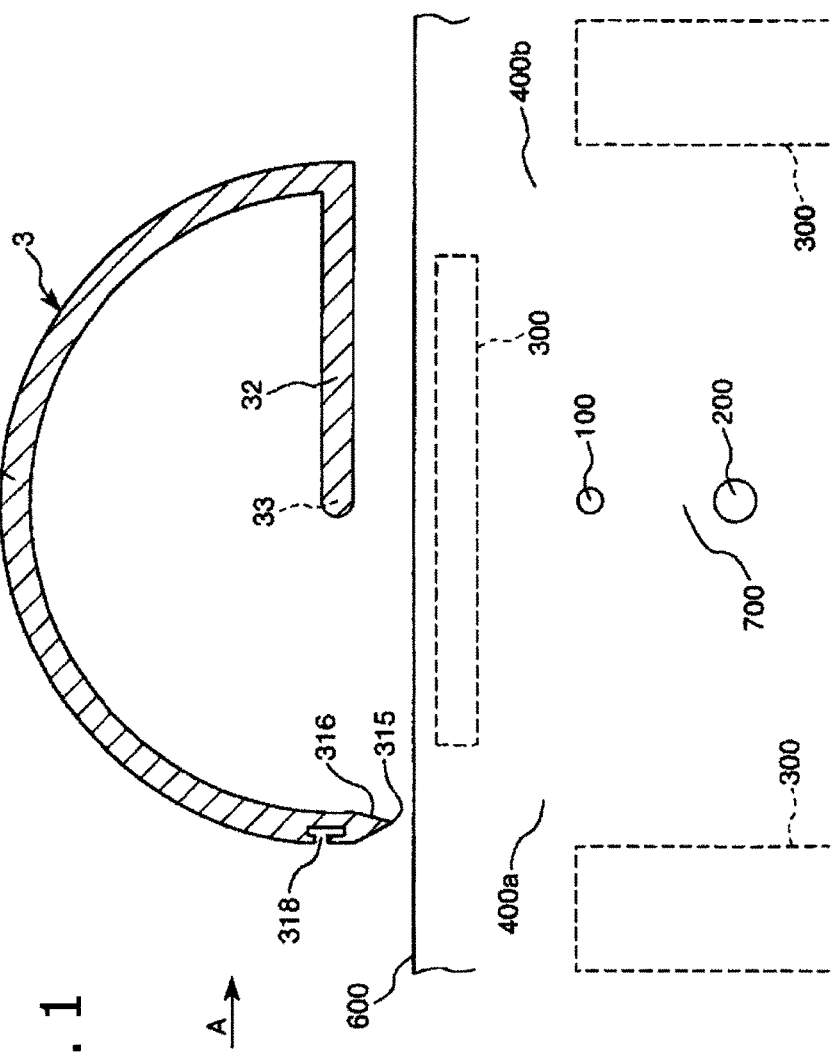
FIG. 1 is a sectional view for sequentially illustrating an exemplary method of using a puncture needle assembly according to a first embodiment of the present disclosure.

First, as shown in FIG. 1, the puncture device 10 is mounted to a body surface 600 of a patient. The mounting position in this instance can be a position suitable for supporting by the urethra 100 the implant 8, which is to be embedded.

Figure 2:
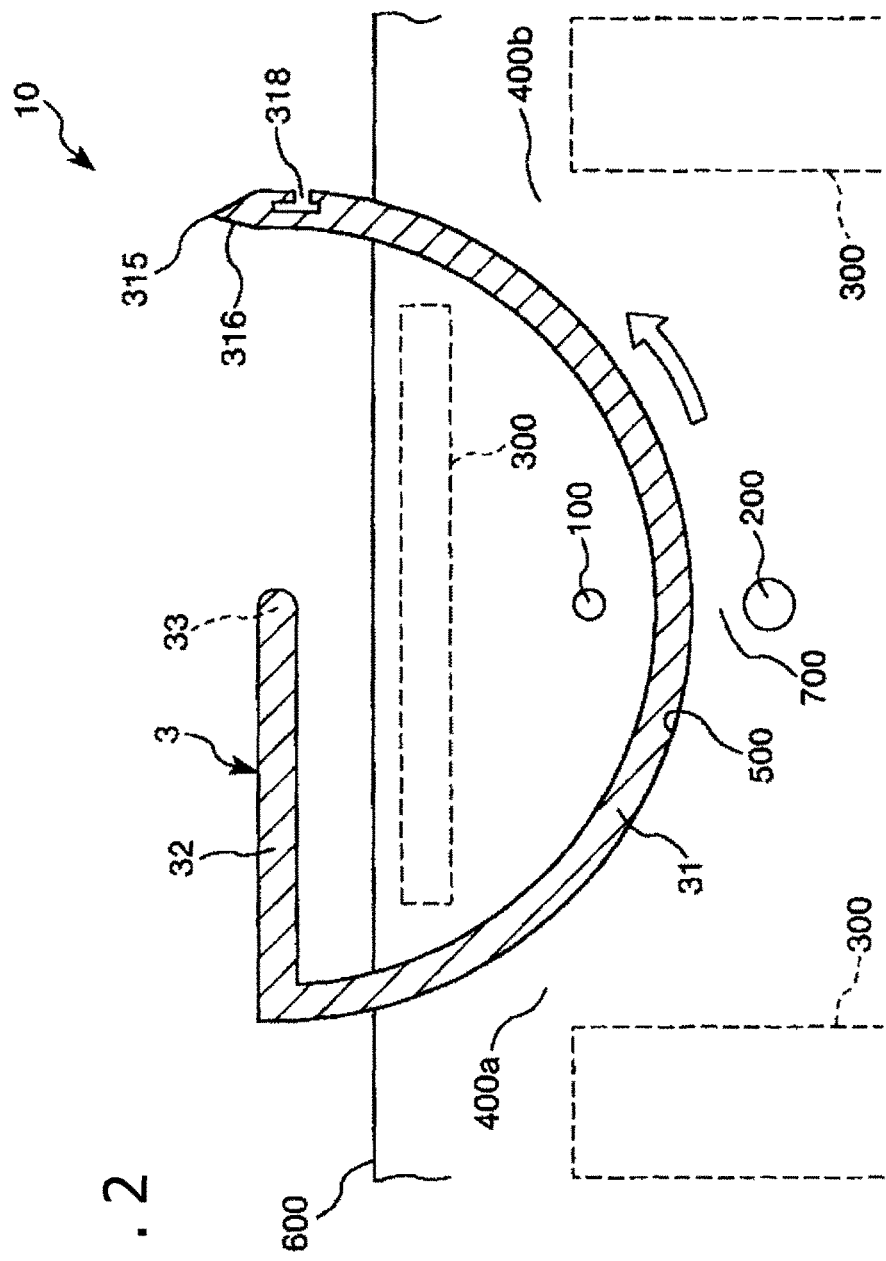
FIG. 2 is a sectional view for sequentially illustrating the method of using the puncture needle assembly according to the first embodiment.

Next, the grip section 34 of the puncture device 10 is gripped by one hand, and, as shown in FIG. 2, the puncture member 3 is rotated counterclockwise in the figure, which causes the puncture needle 31 to move, with the shaft section 33 as a center of turning, so as to sequentially pass, or puncture, a left-side inguinal region (or a part in the vicinity thereof) of the patient's body surface 600, an obturator foramen 400a in a pelvis 300, a region between the urethra 100 and the vagina 200, an obturator foramen 400b in the pelvis 300, and a right-side inguinal region (or a part in the vicinity thereof) of the body surface 600. This puncture forms the piercing hole 500, which penetrates the biological tissue 700 from the left-side inguinal region of the body surface 600 to the right-side inguinal region of the body surface 600. In accordance with an exemplary embodiment, the connection section 317 of the puncture needle 31 is protruding from the right-side inguinal region of the body surface 600.

Subsequently, the connector assembly 2 is provided. As shown in FIG. 3, the connector 4 and the puncture needle 31 are connected by the connection mechanism 6.

In this instance, first, as shown in FIG. 12A, the needle tip section of the puncture needle 31 is inserted into the hole 45 of the connector 4 from the lower side in FIG. 12A. In this case, it can help ensure that the entrance 318c side of the recess 318 of the puncture needle 31 is oriented to the upper side in FIG. 12A. In addition, a portion of the connector 4, which is on the distal side of the projecting piece 43 is inserted into the recess 318 of the puncture needle 31.

Next, as shown in FIG. 12B, the connector assembly 2 is moved (pulled) distally in relation to the puncture needle 31, and is rotated a predetermined angle clockwise in FIG. 12B. Then, as shown in FIG. 12C, the connector assembly 2 is further moved distally in relation to the puncture needle 31. In this instance, the arm sections 431 of the projecting piece 43 of the connector 4 are once broadened by curving in directions for spacing apart from each other, are thereafter inserted into the recess 318, and are restored into their original shapes in their natural state.

As a result, the projecting piece 43 and the recess 318 engage with each other, the puncture needle 31 and the connector 4 are connected to each other, and the connected state is maintained. In addition, the puncture needle 31 and the connector 4 are so connected that the positional relation of the puncture needle 31 and the connector 4 in the direction of rotation about the axis is kept constant.

In the connected state of the puncture needle 31 and the connector 4 depicted in FIG. 12C, the lower surface 433 and the upper surface 434 of the projecting piece 43 respectively make contact with the bottom surface 318a and the ceiling surface 318b of the recess 318 of the puncture needle 31, whereby the connector 4 is inhibited from rotating about the axis in relation to the puncture needle 31. In accordance with an exemplary embodiment, the claws 432 of the arm sections 431 of the projecting piece 43 make contact with proximal-side parts of the ceiling surface 318b of the recess 318, whereby unintentional release of the connected state of the puncture needle 31 and the connector 4 is prevented from occurring.

As aforementioned, in the operation of connecting the puncture needle 31 and the connector 4, the connector assembly 2 is finally moved distally in relation to the puncture needle 31 so as thereby to connect the puncture needle 31 and the connector 4. Therefore, the puncture needle 31 protruding to the exterior from the body surface 600 can be prevented from entering into the body.

Subsequently, the grip section 34 of the puncture device 10 is gripped with one hand, and, as shown in FIG. 4, the puncture member 3 is rotated reversely to the above, namely, clockwise in the figure. As a result, the puncture member 3 is pulled out of the piercing hole 500; in addition, that part of the biological tissue 700 which has been punctured by the puncture needle 31 is dissected by the dissecting section 42 of the connector 4, whereby the piercing hole 500 is broadened, and, this time, the connector assembly 2 is inserted in and passed through the broadened piercing hole 500. In addition, the connector assembly 2 is put in a state wherein a distal-side part of the sheath 5 protrudes from side of the obturator foramen 400b of the body surface 600 and wherein proximal-side parts of the connector 4 and the sheath 5 protrude from the side of the obturator foramen 400a of the body surface 600 (see FIG. 5). Note that while the implant 8 is preliminarily inserted in the sheath 5 in this embodiment, for example in the case where the implant 8 is not preliminarily inserted in the sheath 5, the implant 8 is then inserted in the sheath 5 and is inserted (introduced) into the body through the sheath 5. In this case, the sheath 5 constitutes the elongated body of the puncture needle assembly 1.

Next, as shown in FIG. 5, a proximal-side part of the sheath 5 of the connector assembly 2 and a proximal-side part of the implant 8 are cut, and the puncture member 3 of the puncture device 10 is removed together with the support member 20 from the body surface 600. In this instance, the connector 4 is removed together with the puncture member 3.

Figure 6:
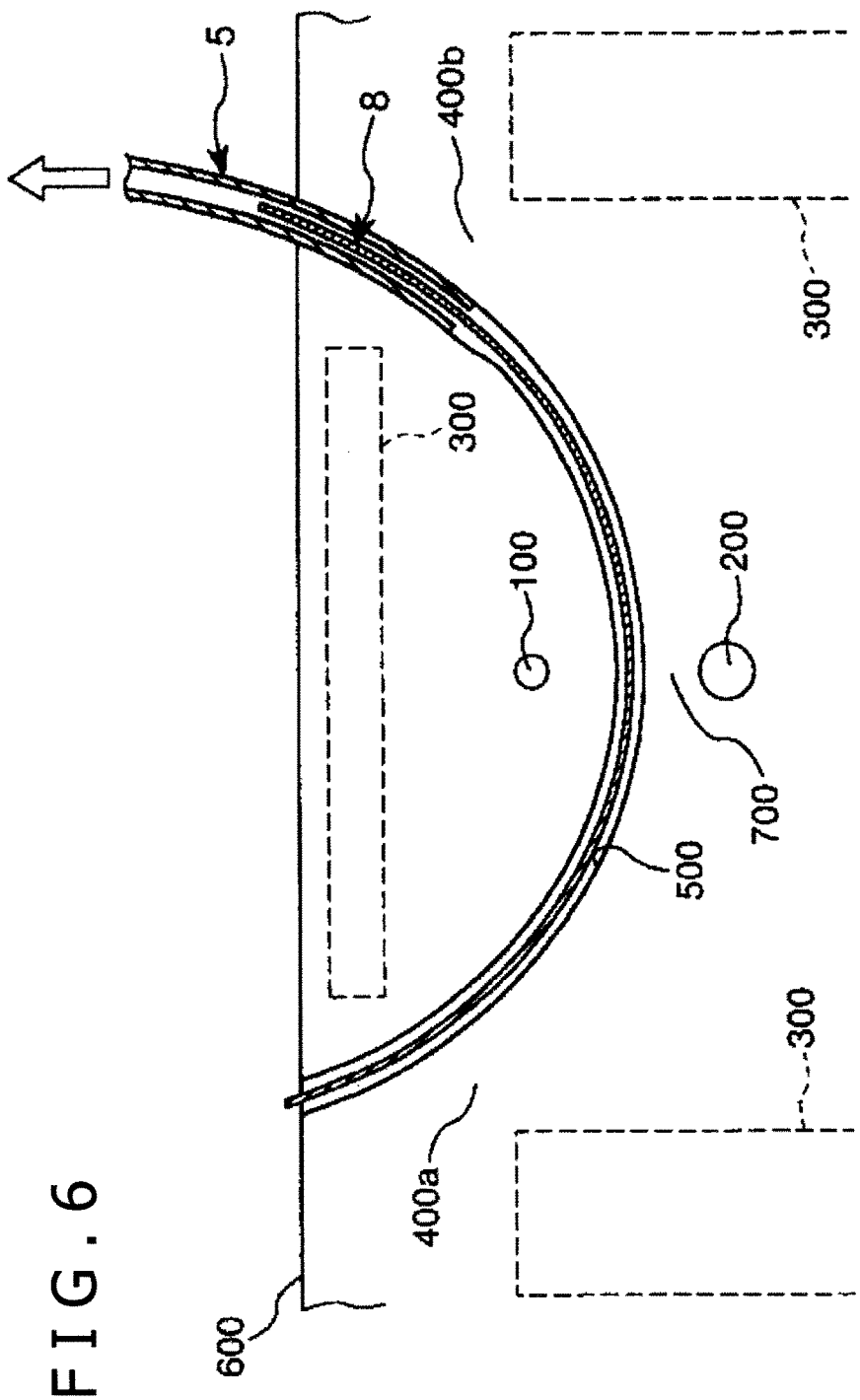
FIG. 6 is a sectional view for sequentially illustrating the method of using the puncture needle assembly according to the first embodiment.
Figure 7:
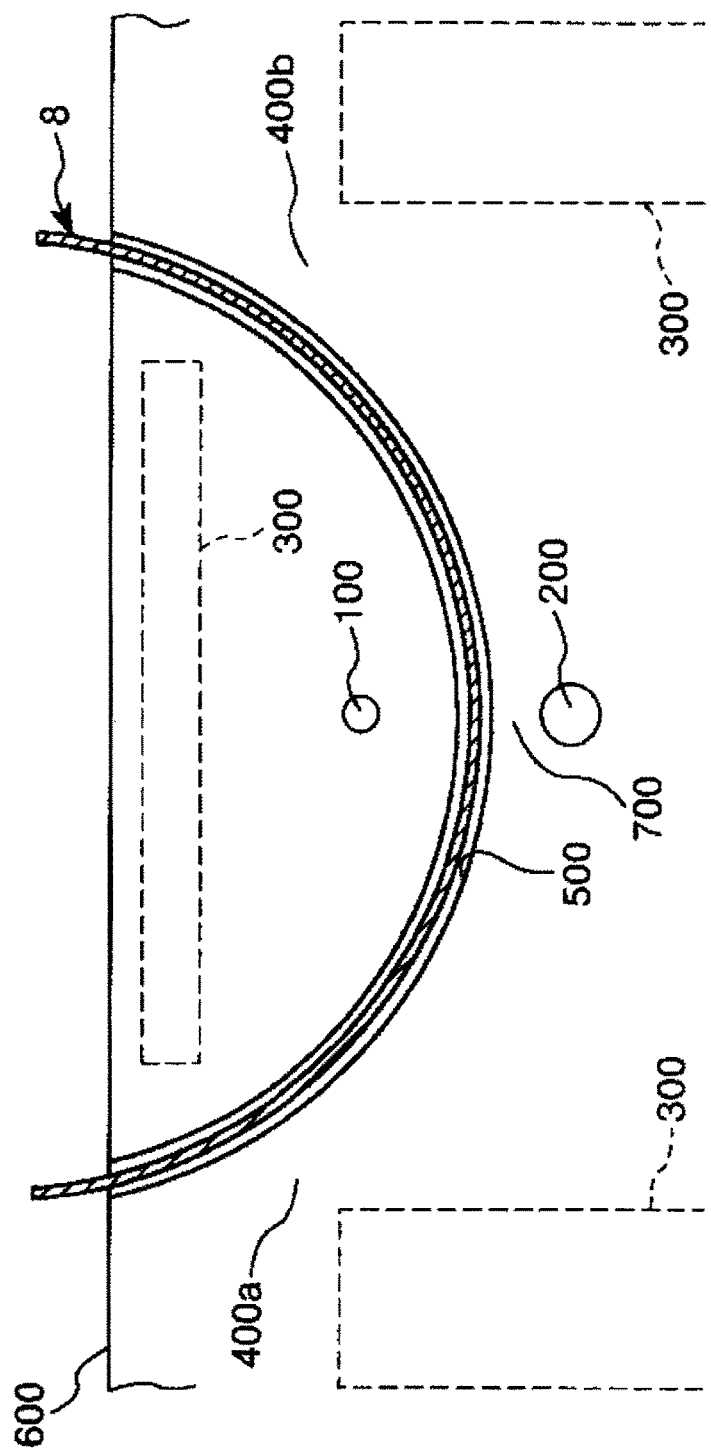
FIG. 7 is a sectional view for sequentially illustrating the method of using the puncture needle assembly according to the first embodiment.

Subsequently, that portion of the sheath 5 which protrudes from the side of the obturator foramen 400b of the body surface 600 is gripped with one hand, that portion of the implant 8 which protrudes from the side of the obturator foramen 400a of the body surface 600 is gripped with the other hand, and, as shown in FIG. 6, the sheath 5 is pulled proximally out of the piercing hole 500. As a result, the implant 8 is left inserted in and extending through the piercing hole 500, as shown in FIG. 7. The implant 8 is in the state where its distal-side portion is protruding from the side of the obturator foramen 400b of the body surface 600 and its proximal-side portion is protruding from the side of the obturator foramen 400a of the body surface 600. Then, the distal-side portion and the proximal-side portion of the implant 8 can be pulled respectively with predetermined forces, to adjust the position of the implant 8 relative to the urethra 100. Note that in this instance a tension may be generated on the implant 8. As a result, the urethra 100 is supported from below by the implant 8 so that its movement in the direction of coming away from the vagina 200 is restricted; in some cases, the urethra 100 is pulled away from the vagina 200 and is supported from below by the implant 8.

Figure 8:
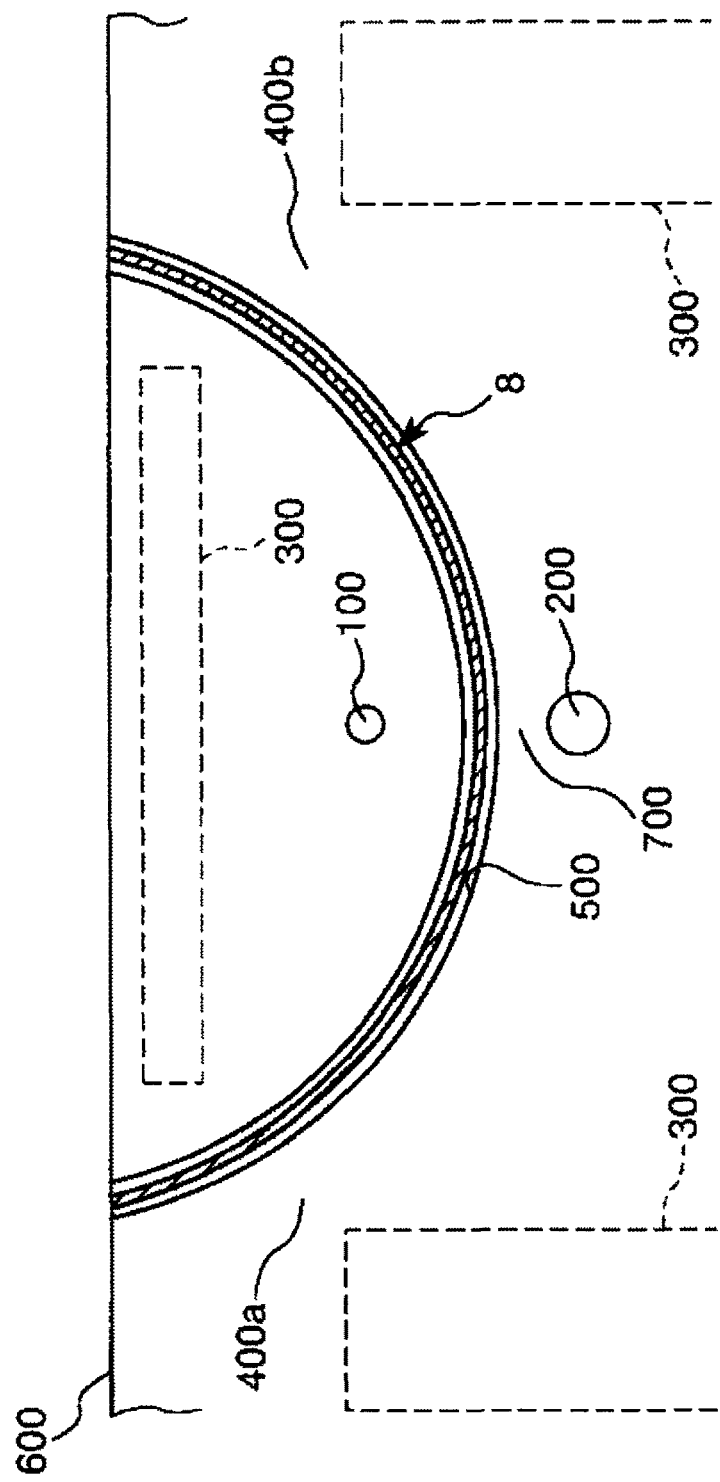
FIG. 8 is a sectional view for sequentially illustrating the method of using the puncture needle assembly according to the first embodiment.
Figure 9:
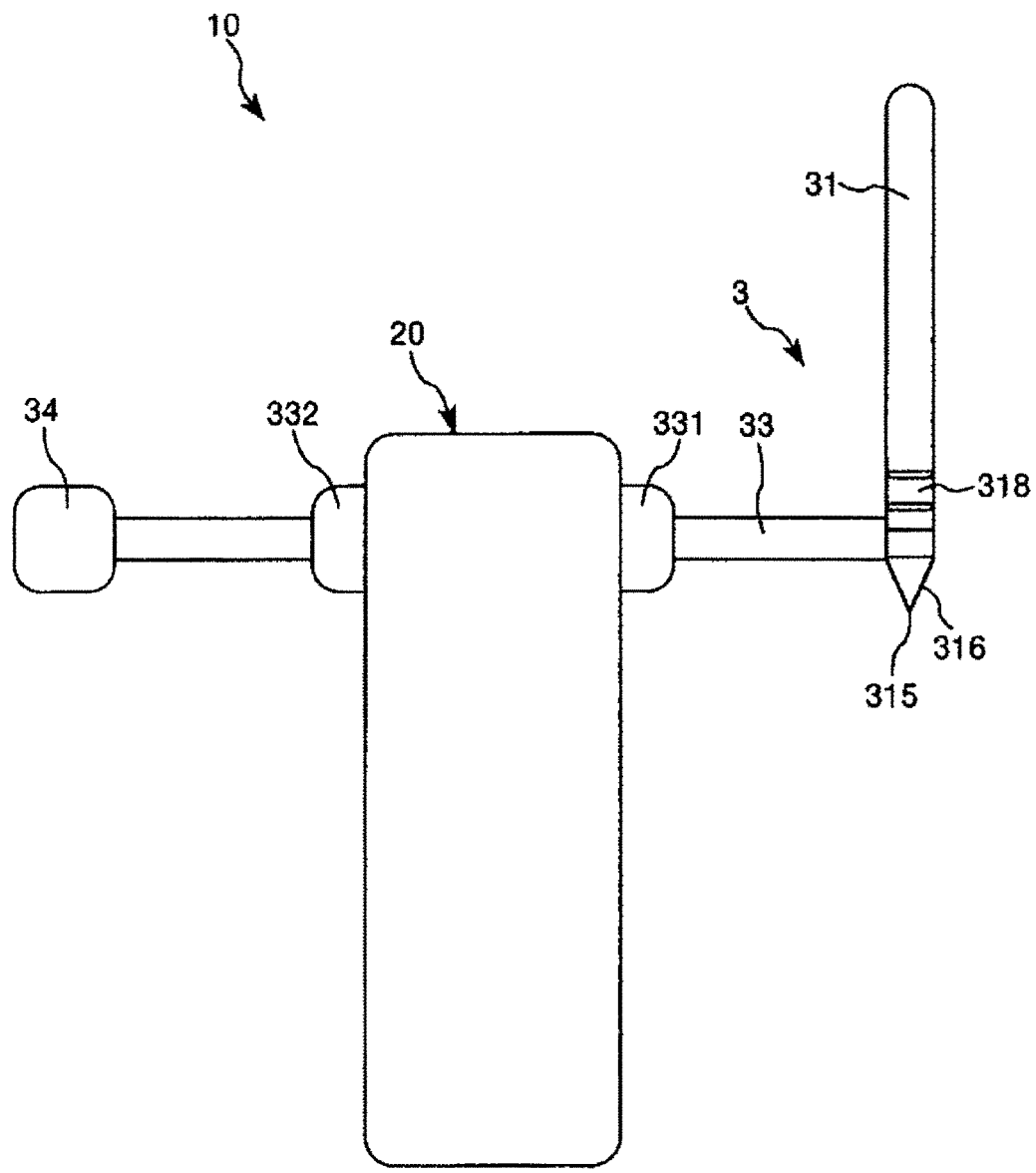
FIG. 9 is a side view as viewed in the direction of arrow A in FIG. 1.

Next, as shown in FIG. 8, unnecessary portions of the implant 8 are cut away, and predetermined wound closure and the like are conducted to complete the procedure.

As aforementioned, according to this puncture needle assembly 1, at the time of embedding the implant 8 in the body in the state of being in a predetermined orientation, it is possible to meet the requirement with only low-invasive procedures such as puncture of the biological tissue by the puncture needle 31 and the dissection of the biological tissue by the dissecting section 42, without need for any high-invasive procedure such as incision of vaginal wall. Therefore, the burden on the patient can be relatively low, and the safety of the patient can be relatively high. In addition, the problems often encountered in the case of incising the vaginal wall can be prevented, such as the exposure of the implant 8 to the inside of the vagina through the wound formed by incision or the generation of complications such as an infection via the wound. Thus, very high safety can be relatively ensured and the implant 8 can be embedded relatively reliably.

In embedding the implant 8, the biological tissue is punctured by the puncture needle 31, and the biological tissue is dissected by the dissecting section 42, to form the piercing hole 500. Therefore, the operation of embedding the implant 8 can be performed relatively easily and reliably.

For example, the biological tissue can be dissected in a width approximately equal to the width of the implant 8 by the dissecting section 42. Therefore, the implant 8 can be embedded relatively assuredly by a very low invasive procedure.

The puncture needle 31 and the connector 4 can be connected so that the positional relation of the puncture needle 31 and the connector 4 in the direction of rotation about the axis is kept constant, and the rotation of the connector 4 about the axis in relation to the puncture needle 31 in the connected state is restricted. Therefore, the implant 8 can be embedded to be oriented in the intended orientation.

The operator need not perform incision or the like, so that injuring fingertips with a surgical knife or the like can be prevented from occurring, and safety is ensured.

Figures 13A, 13B:
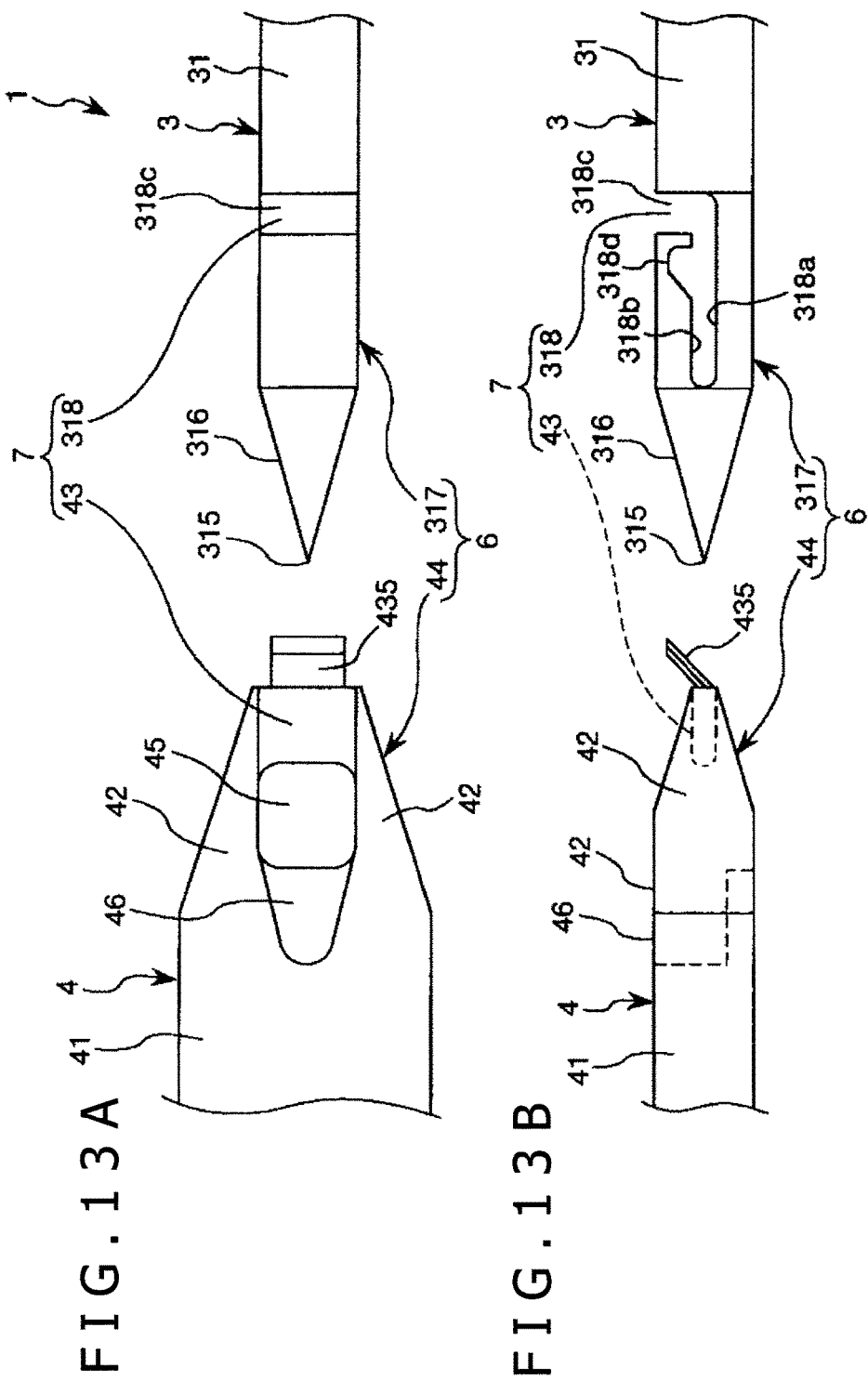
FIGS. 13A and 13B illustrate a portion of a puncture needle assembly according to a second embodiment of the present disclosure.
Figure 14:
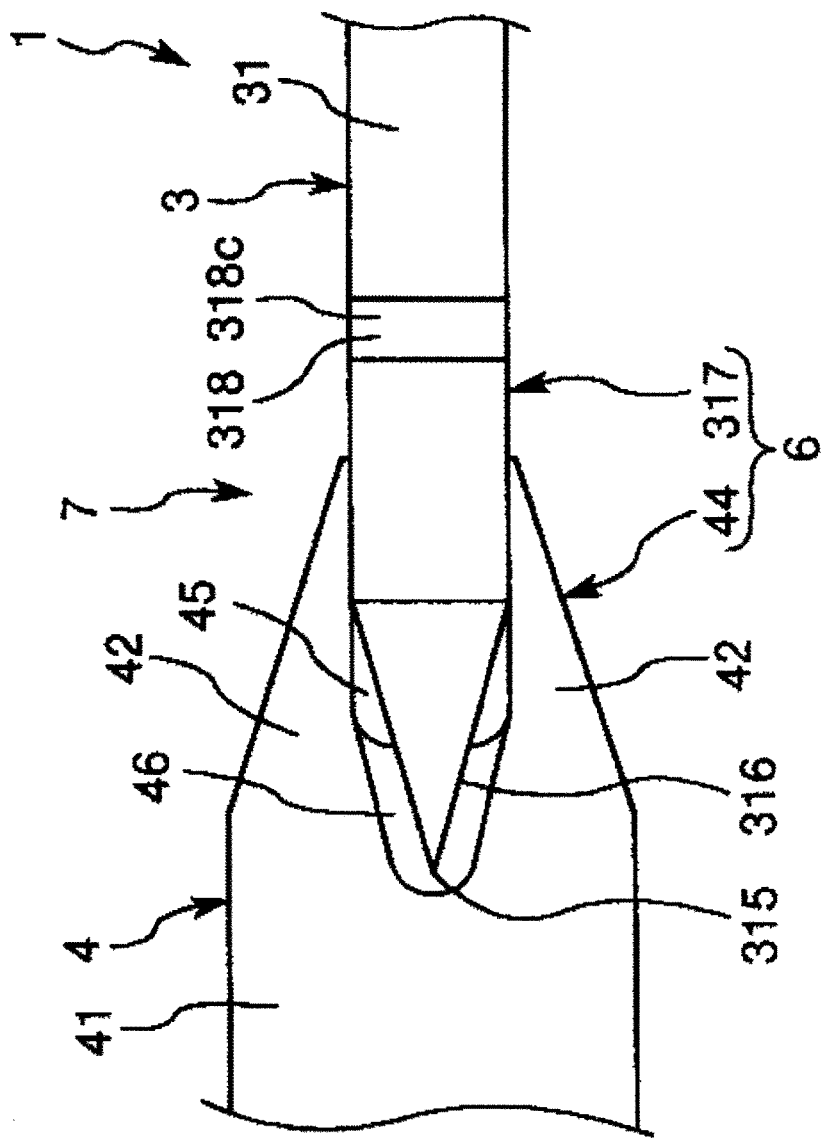
FIG. 14 is a plan view showing a connected state in which a puncture needle and a connector of the puncture needle assembly shown in FIGS. 13A and 13B are connected.
Figure 15A:
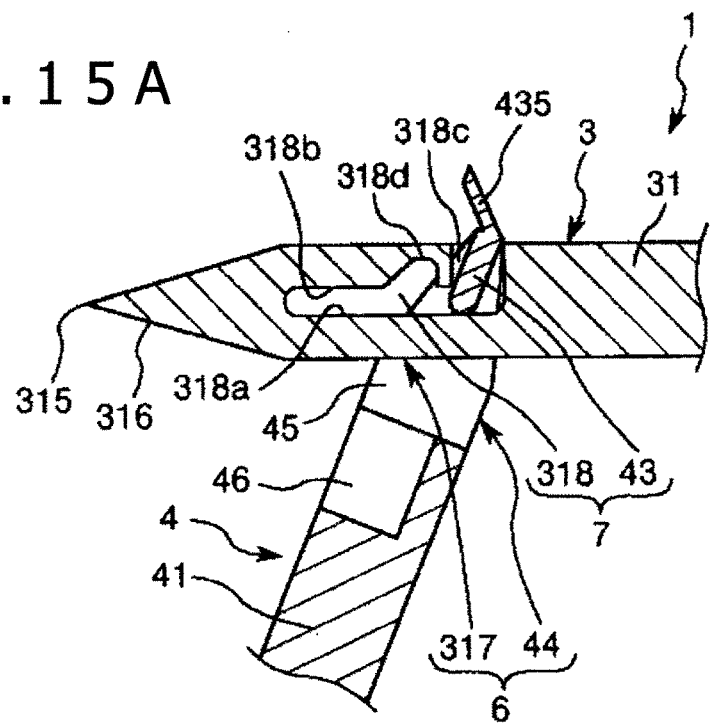
FIGS. 15A and 15B are sectional views illustrating a procedure for connecting the puncture needle and the connector of the puncture needle assembly shown in FIGS. 13A and 13B.
Figure 15B:
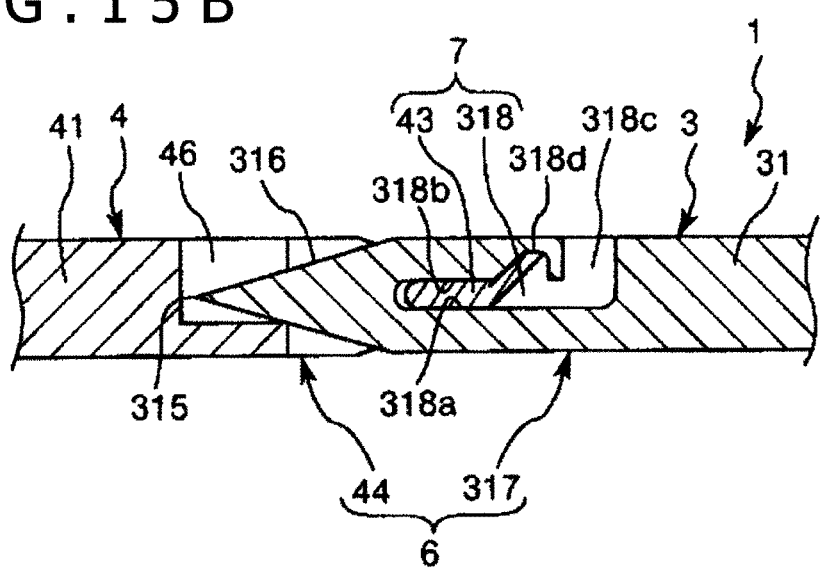

FIGS. 13A and 13B illustrate a portion of a puncture needle assembly according to a second embodiment of the present disclosure, wherein FIG. 13A is a plan view and FIG. 13B is a sectional view. FIG. 14 is a plan view showing a connected state in which a puncture needle and a connector of the puncture needle assembly shown in FIGS. 13A and 13B are connected. FIGS. 15A and 15B are sectional views illustrating a procedure for connecting the puncture needle and the connector of the puncture needle assembly shown in FIGS. 13A and 13B. In the following, for convenience of explanation, the needle tip side will be referred to as the "distal" side and the opposite side as the "proximal" side.

The second embodiment will be described below, referring primarily to differences from the aforementioned first embodiment, and while omitting descriptions of the same items as above.

As shown in FIGS. 13A, 13B and 14, in a puncture needle assembly 1 in the second embodiment, a projecting piece 43 of a connector 4 is provided at a proximal portion thereof with a bent section 435 which is bent to the upper side in FIG. 13B and is elastic.

A connection section 317 of a puncture needle 31 is provided, at a ceiling surface 318b of a recess 318, with a recess (second recess) 318d as a contact section for contact with the bent section 435 in a connected state of the puncture needle 31 and the connector 4.

At the time of connecting the connector 4 and the puncture needle 31 by a connection mechanism 6, first, as shown in FIG. 15A, a needle tip section of the puncture needle 31 is inserted in a hole 45 in the connector 4 from the lower side in FIG. 15A. In this case, it can help ensure that an entrance 318c side of the recess 318 of the puncture needle 31 is oriented toward the upper side in FIG. 15A. In addition, a distal-side portion of a projecting piece 43 of the connector 4 is inserted into the recess 318 of the puncture needle 31.

Next, as shown in FIG. 15B, a connector assembly 2 is moved distally in relation to the puncture needle 31, and is rotated a predetermined angle clockwise in FIG. 15B. In this instance, the bent section 435 of the projecting piece 43 of the connector 4 is once deformed so as to reduce its degree of bending, and is thereafter inserted into the recess 318d, to be restored into its original shape in its natural state.

As a result, the projecting piece 43 and the recess 318 are engaged with each other, the puncture needle 31 and the connector 4 are connected, and the connected state is maintained. In addition, the puncture needle 31 and the connector 4 are connected so that the positional relation of the puncture needle 31 and the connector 4 in the direction of rotation about the axis is kept constant.

In the connected state of the puncture needle 31 and the connector 4 shown in FIG. 15B, a lower surface 433 and an upper surface 434 of the projecting piece 43, respectively, make contact with a bottom surface 318a and the ceiling surface 318b of the recess 318 of the puncture needle 31, whereby the connector 4 is inhibited from rotating about the axis in relation to the puncture needle 31.

The bent section 435 is inserted into the recess 318d, and makes contact with an inner surface of the recess 318d, whereby unintentional release of the connected state of the puncture needle 31 and the connector 4 can be securely prevented from occurring. Note that the bent section 435 and the recess 318d constitute a connection release preventing mechanism.

According to this puncture needle assembly 1, the same or equivalent effects to those of the aforementioned first embodiment can be obtained.

Figures 16A, 16B:
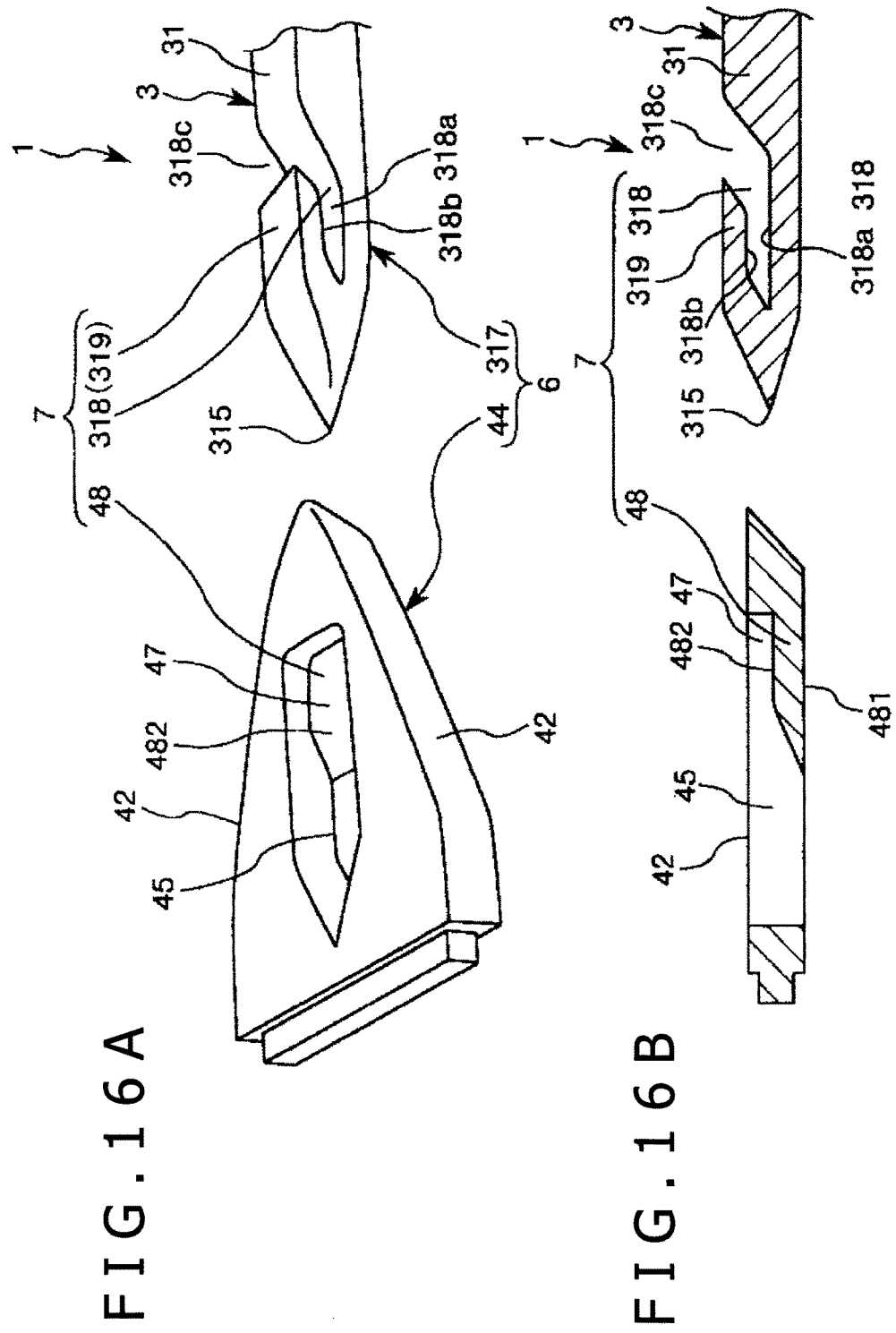
FIGS. 16A and 16B illustrate a portion of a puncture needle assembly according to a third embodiment of the present disclosure.

FIGS. 16A and 16B illustrate a portion of a puncture needle assembly according to a third embodiment of the present disclosure, wherein FIG. 16A is a perspective view and FIG. 16B is a sectional view. In the following, for convenience of explanation, the upper side in FIGS. 16A and 16B will be referred to as "upper" or "upper side," and the lower side as "lower" or "lower side." In addition, the needle tip side will be referred to as "distal" side, and the opposite side as "proximal" side.

The third embodiment will be described below, referring primarily to differences from the aforementioned first embodiment, and while omitting descriptions of the same items as above.

As shown in FIGS. 16A and 16B, in a puncture needle assembly 1 in the third embodiment, due to the presence of a recess 318, a hook (projection) 319 projecting toward the proximal side is formed on a connection section 317 of a puncture needle 31.

A main body section 41 of a connector 4 is formed, on the proximal side of a hole 45, with a recess 47 communicating with the hole 45. Due to the presence of the recess 47, a thin-walled section (connector-side engaging section) 48 is formed. Note that the recess 47 is opening to the upper side in FIG. 16B.

In the connected state of the puncture needle 31 and the connector 4, the thin-walled section 48 and the recess 318 (hook 319) are engaged.

In the connected state of the puncture needle 31 and the connector 4, a lower surface 481 and an upper surface 482 of the thin-walled section 48 respectively make contact with a bottom surface 318a and a ceiling surface 318b of the recess 318 in the puncture needle 31, whereby the connector 4 is inhibited from rotating about the axis in relation to the puncture needle 31.

According to this puncture needle assembly 1, the same or equivalent effects to those of the aforementioned first embodiment can be obtained.

In this puncture needle assembly 1, a connection release preventing mechanism for preventing the connected state of the puncture needle 31 and the connector 4 from being released is omitted. Therefore, the connected state of the puncture needle 31 and the connector 4 can be easily released.

Note that in each of fourth to tenth embodiments, which will be, described later, the connection release preventing mechanism is provided, whereby unintentional release of the connected state of the puncture needle 31 and the connector 4 can be securely prevented from occurring.

Figure 17:
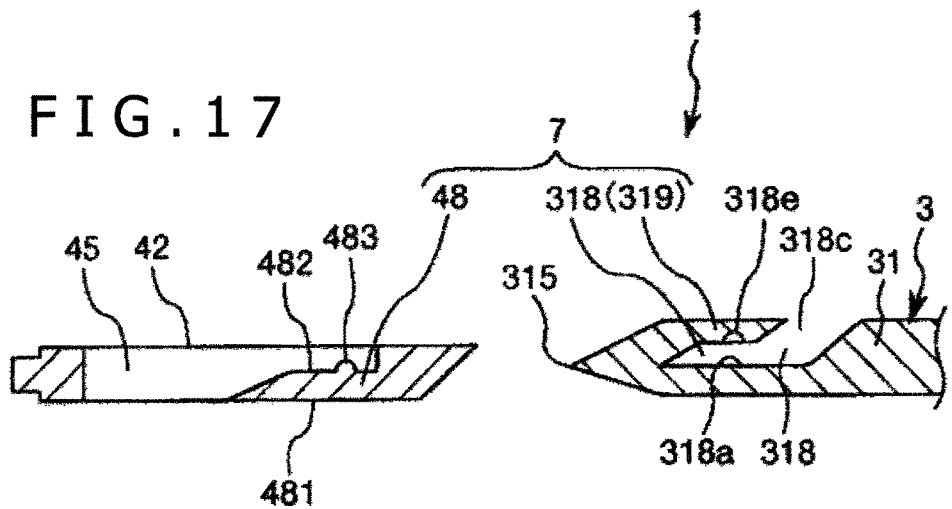
FIG. 17 is a sectional view showing a portion of a puncture needle assembly according to a fourth embodiment of the present disclosure.

FIG. 17 is a sectional view showing a portion of a puncture needle assembly according to a fourth embodiment of the present disclosure. In the following, for convenience of explanation, the upper side in FIG. 17 will be referred to as "upper" or "upper side," and the lower side as "lower" or "lower side." Besides, the needle tip side will be referred to as "distal" side, and the opposite side as "proximal" side.

The fourth embodiment will be described below, referring primarily to differences from the aforementioned third embodiment, and while omitting descriptions of the same items as above.

As shown in FIG. 17, in a puncture needle assembly 1 in the fourth embodiment, a ceiling surface 318b of a recess 318 (hook 319) of a puncture needle 31 is formed with a recess (second recess) 318e.

In addition, an upper surface 482 of a thin-walled section 48 of a connector 4 is formed with a projection 483 for engagement with the recess 318e of the puncture needle 31 in a connected state of the puncture needle 31 and the connector 4. By this, unintentional release of the connected state of the puncture needle 31 and the connector 4 can be securely prevented from occurring.

According to this puncture needle assembly 1, the same or equivalent effects to those of the aforementioned third embodiment can be obtained.

Figure 18:
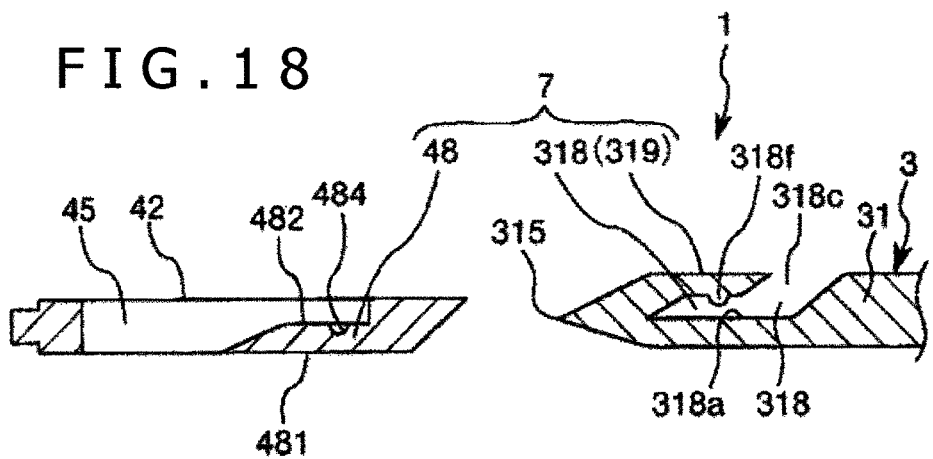
FIG. 18 is a sectional view showing a portion of a puncture needle assembly according to a fifth embodiment of the present disclosure.

FIG. 18 is a sectional view showing a portion of a puncture needle assembly according to a fifth embodiment of the present disclosure. In the following, for convenience of explanation, the upper side in FIG. 18 will be referred to as "upper" or "upper side," and the lower side as "lower" or "lower side." Besides, the needle tip side will be referred to as "distal" side, and the opposite side as "proximal" side.

The fifth embodiment will be described below, referring primarily to differences from the aforementioned third embodiment, and while omitting descriptions of the same items as above.

As shown in FIG. 18, a puncture needle assembly 1 in the fifth embodiment, an upper surface 482 of a thin-walled section 48 of a connector 4 is formed with a recess (second recess) 484.

In addition, a ceiling surface 318b of a recess 318 (hook 319) of a puncture needle 31 is formed with a projection 318f for engagement with the recess 484 of the puncture needle 31 in a connected state of the puncture needle 31 and the connector 4. By this, unintentional release of the connected state of the puncture needle 31 and the connector 4 can be securely prevented from occurring.

According to this puncture needle assembly 1, the same or equivalent effects to those of the aforementioned third embodiment can be obtained.

Figure 19:
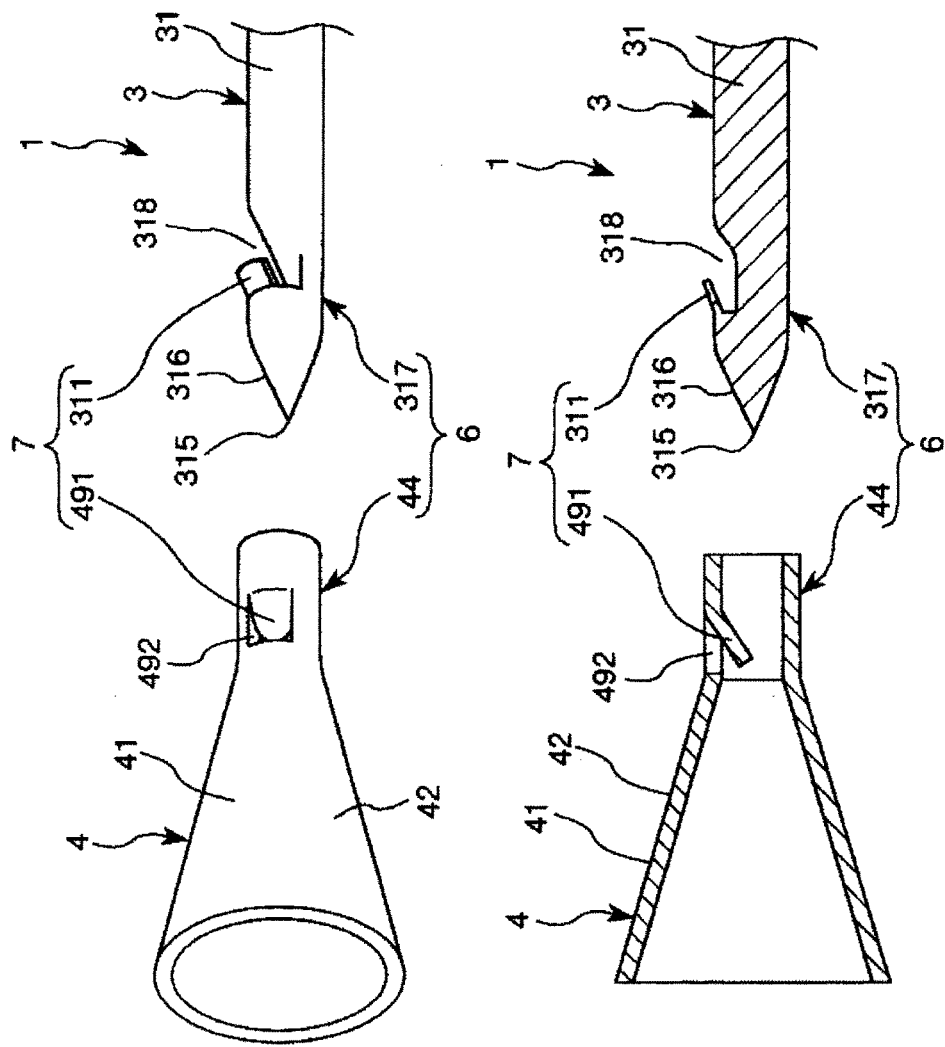
FIGS. 19A and 19B illustrate a portion of a puncture needle assembly according to a sixth embodiment of the present disclosure.

FIGS. 19A and 19B illustrate a portion of a puncture needle assembly according to a sixth embodiment of the present disclosure, wherein FIG. 19A is a perspective view and FIG. 19B is a sectional view. In the following, for convenience of explanation, the upper sides in FIGS. 19A and 19B will each be referred to as "upper" or "upper side," and the lower side as "lower" or "lower side." In addition, the needle tip side will be referred to as "distal" side, and the opposite side as "proximal" side.

The sixth embodiment will be described below, referring primarily to differences from the aforementioned first embodiment, and while omitting descriptions of the same items as above.

As shown in FIGS. 19A and 19B, a puncture needle assembly 1 in the sixth embodiment, a puncture needle 31 is provided at a needle tip section of the puncture needle 31 with a projecting piece (puncture needle-side projecting piece) 311 which is elastic and projects toward the proximal side in the axial direction, as a first rotation restricting section. The projecting piece 311 is formed at an upper end part of a distal portion of a recess 318.

A main body section 41 of a connector 4 is tubular in shape. For example, the main body section 41 of the connector 4 is formed, at a proximal portion of the main body section 41, with a connection section 44 as a tubular section into which a needle tip section of the puncture needle 31 is to be inserted. Note that in this embodiment, the main body section 41 is circular in cross section.

The connection section 44 has a projecting piece (connector-side projecting piece) 491 which is elastic and projects toward the distal side in the axial direction, as a connector-side engaging section. The projecting piece 491 is formed by forming a U-shaped (approximately rectangular U-shaped) slit 492 which penetrates a tubular wall of the main body section 41, and bending inward the part surrounded by the slit 492. Note that in FIGS. 19A and 19B, the slit 492 is so disposed that the opening of the U shape of the slit 492 is oriented toward the proximal side (the right side in FIGS. 19A and 19B).

At the time of connecting the connector 4 and the puncture needle 31 by a connection mechanism 6, a needle tip section of the puncture needle 31 is inserted into the connection section 44 in a condition where the positions in the circumferential direction of the projecting piece 491 and the recess 318 (projecting piece 311) coincide with each other.

In the connected state of the puncture needle 31 and the connector 4, the projecting piece 491 is in engagement with the recess 318, whereby the connected state is maintained securely.

The projecting piece 491 can also function as a second rotation restricting section. In the connected state of the puncture needle 31 and the connector 4, an outer surface of the projecting piece 491 and an inner surface of the projecting piece 311 are in contact with each other, whereby the connector 4 is inhibited from rotating about the axis in relation to the puncture needle 31.

According to this puncture needle assembly 1, the same or equivalent effects to those of the aforementioned first embodiment can be obtained.

Figure 20:
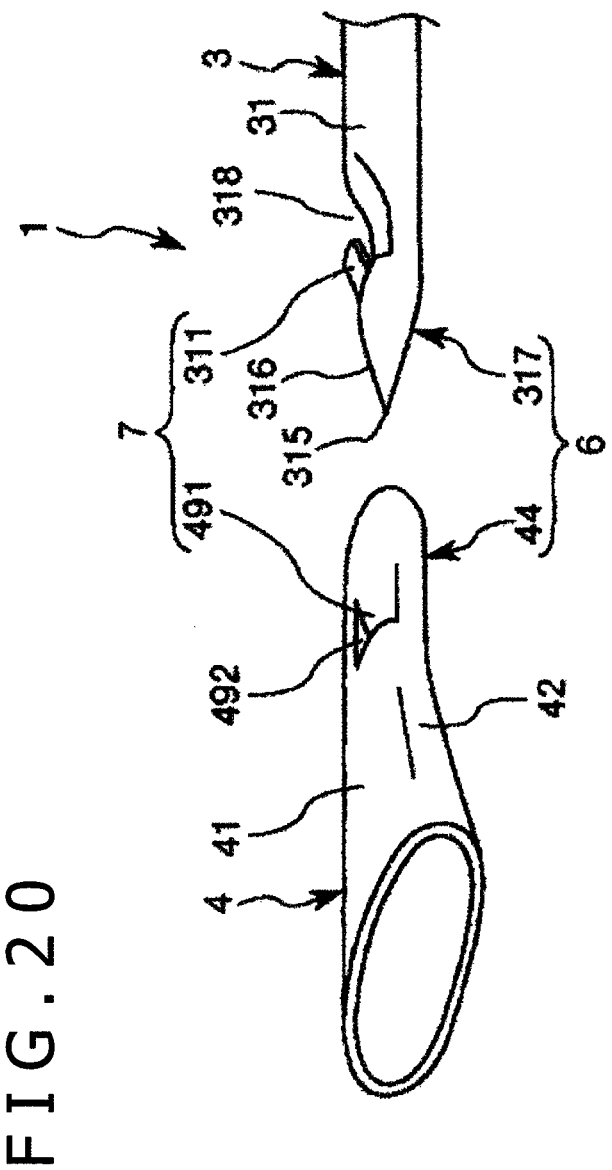
FIG. 20 is a perspective view showing a portion of a puncture needle assembly according to a seventh embodiment of the present disclosure.

FIG. 20 is a perspective view showing a portion of a puncture needle assembly according to a seventh embodiment of the present disclosure. In the following, for convenience of explanation, the upper side in FIG. 20 will be referred to as "upper" or "upper side," and the lower side as "lower" or "lower side." Besides, the needle tip side will be referred to as "distal" side, and the opposite side as "proximal" side.

The seventh embodiment will be described below, referring primarily to differences from the aforementioned sixth embodiment, and while omitting descriptions of the same items as above.

As shown in FIG. 20, in a puncture needle assembly 1 in the seventh embodiment, a main body section 41 of a connector 4 is flat-shaped, for example, elliptic in cross section. A surface on the side of a minor diameter of the flat shape (a surface on the upper side in FIG. 20) of the main body section 41 is formed with a projecting piece 491.

A puncture needle 31 is flat-shaped, for example, elliptic in cross section. A surface on the side of a minor diameter of the flat shape (a surface on the upper side in FIG. 20) of the puncture needle 31 is formed with a recess 318 and a projecting piece 311.

According to this puncture needle assembly 1, the same or equivalent effects to those of the aforementioned sixth embodiment can be obtained.

Figure 21:
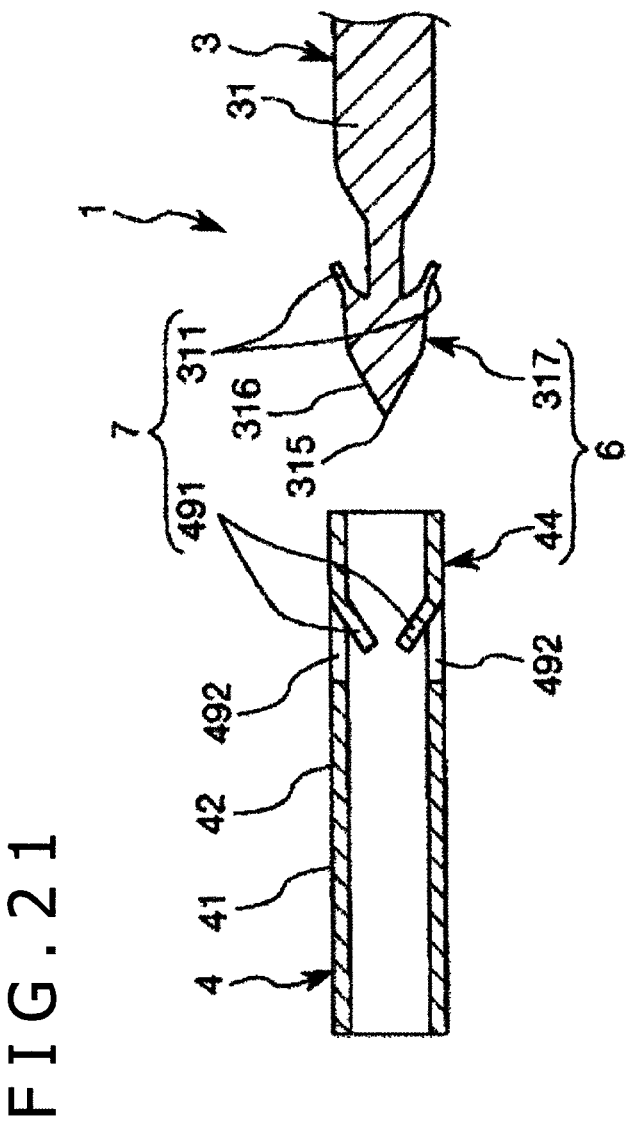
FIG. 21 is a sectional view showing a portion of a puncture needle assembly according to an eighth embodiment of the present disclosure.

FIG. 21 is a sectional view showing a portion of a puncture needle assembly according to an eighth embodiment of the present disclosure. In the following, the upper side in FIG. 21 will be referred to as "upper" or "upper side," and the lower side as "lower" or "lower side." In addition, the needle tip side will be referred to as "distal" side, and the opposite side as "proximal" side.

The eighth embodiment will be described below, referring primarily to differences from the aforementioned seventh embodiment, and while omitting descriptions of the same items as above.

As shown in FIG. 21, in a puncture needle assembly 1 in the eighth embodiment, a connection section 44 of a connector 4 has a pair of projecting pieces 491 disposed to face each other. A puncture needle 31 has a pair of projecting pieces 311 disposed to be opposite to each other.

According to this puncture needle assembly 1, the same or equivalent effects to those of the aforementioned seventh embodiment can be obtained.

Figure 22:
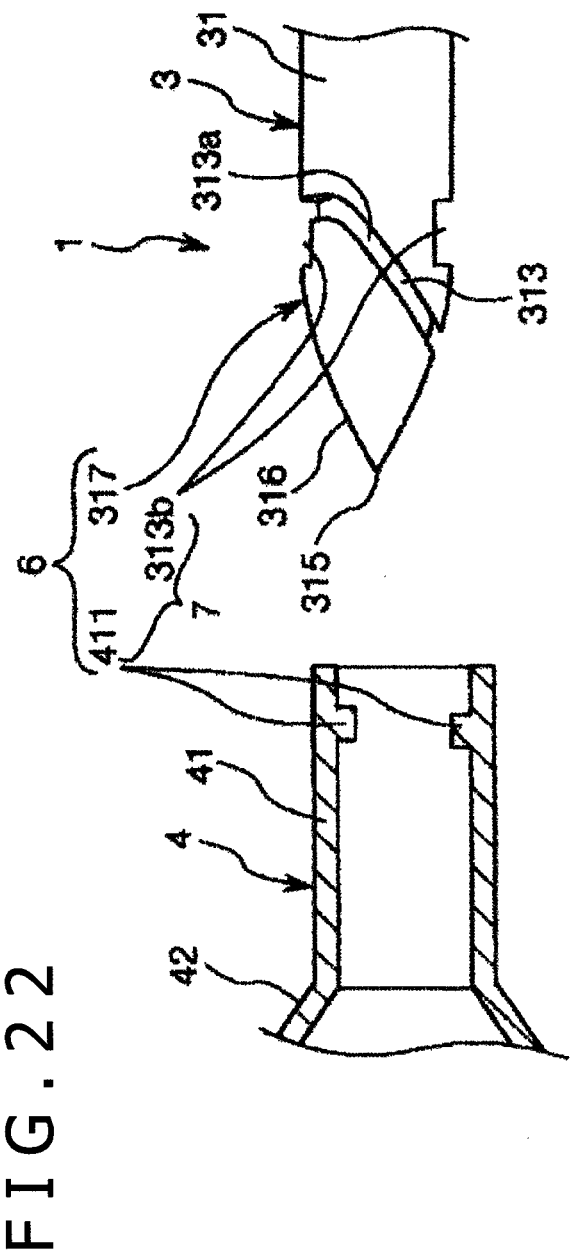
FIG. 22 illustrates a portion of a puncture needle assembly according to a ninth embodiment of the present disclosure.

FIG. 22 illustrates a portion of a puncture needle assembly according to a ninth embodiment of the present disclosure. FIG. 22 is a perspective view for a puncture needle, and is a sectional view for a connector. In the following, for convenience of explanation, the upper side in FIG. 22 will be referred to as "upper" or "upper side," and the lower side as "lower" or "lower side." In addition, the needle tip side will be referred to as "distal" side, and the opposite side as "proximal" side.

The ninth embodiment will be described below, referring primarily to differences from the aforementioned first embodiment, and while omitting descriptions of the same items as above.

As shown in FIG. 22, in a puncture needle assembly 1 in the ninth embodiment, a connection section 317 of a puncture needle 31 is provided, in the peripheral surface of a needle tip section thereof, with a pair of grooves (first connection section) (first rotation restricting section) 313 disposed to be opposite to each other. Each of the grooves 313 is formed to range less than one circumference. In addition, each of the grooves 313 includes a spiral part 313*a*, and a straight part 313*b* extending distally from a proximal end of the spiral part 313*a*.

A main body section 41 of a connector 4 is provided at a proximal portion thereof with a pair of projections (second connection section) (third rotation restricting section) 411 which are to be inserted in the pair of grooves 313 and moved along the pair of grooves 313. The projections 411 are formed at an inner circumferential surface of the main body section 41 so as to face each other.

At the time of connecting the puncture needle 31 and the connector 4, first, a needle tip section of the puncture needle 31 is inserted into the main body section 41 of the connector 4. By this, the projections 411 are inserted into the spiral parts 313*a* of the grooves 313. Then, the connector 4 is rotated in a predetermined direction in relation to the puncture needle 31. By this, the projections 411 are relatively moved along the spiral parts 313*a* of the grooves 313, and, when they have reached end portions of the spiral parts 313*a*, the connector 4 is pulled distally in relation to the puncture needle 31. By this, the projections 411 are relatively moved distally along the straight parts 313*b* of the grooves 313, and, when they have reached end portions of the straight parts 313*b*, the projections 411 and the end portions of the straight parts 313*b* of the grooves 313 are engaged with each other, so that the puncture needle 31 and the connector 4 are connected to each other.

In the connected state of the puncture needle 31 and the connector 4, the projections 411 and the straight parts 313*b* of the grooves 313 are in engagement with each other, whereby the connector 4 is inhibited from rotating about the axis in relation to the puncture needle 31.

According to this puncture needle assembly 1, the same or equivalent effects to those of the aforementioned first embodiment can be obtained.

Note that in the present disclosure, a configuration may be adopted in which grooves are formed on the connector 4 side and projections are formed on the puncture needle 31 side.

Figure 23A:
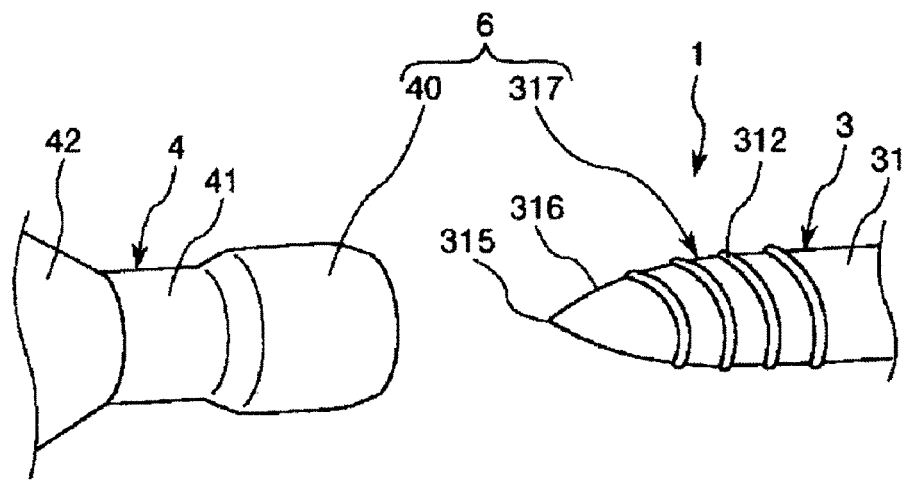
FIGS. 23A and 23B illustrate a portion of a puncture needle assembly according to a tenth embodiment of the present disclosure.
Figure 23B:
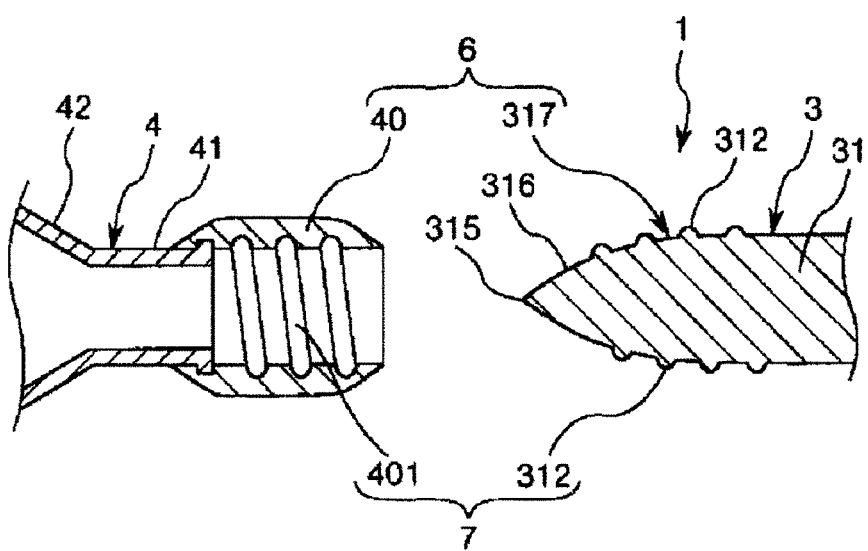

FIGS. 23A and 23B illustrate a portion of a puncture needle assembly according to a tenth embodiment of the present disclosure, wherein FIG. 23A is a perspective view and FIG. 23B is a sectional view. In the following, for convenience of explanation, the upper side in FIGS. 23A and 23B will be referred to as "upper" or "upper side," and the lower side as "lower" or "lower side." Besides, the needle tip side will be referred to as "distal" side, and the opposite side as "proximal" side.

The tenth embodiment will be described below, referring primarily to differences from the aforementioned first embodiment, and while omitting descriptions of the same items as above.

As shown in FIGS. 23A and 23B, in a puncture needle assembly 1 in the tenth embodiment, a connection section 317 of a puncture needle 31 has a male screw (first connection section) (first rotation restricting section) 312 at the peripheral surface of a needle tip section of the puncture needle 31.

A main body section 41 of a connector 4 is tubular in shape. Note that in this embodiment, the main body section 41 is circular in cross section.

The connector 4 is provided, at a distal portion of the main body section 41 thereof, with a rotating tube 40 which is disposed to be able to rotate about the axis thereof but inhibited from moving in the axial direction thereof. The rotating tube 40 is provided, at an inner circumferential surface thereof, with a female screw (second connection section) (second rotation restricting section) 401 for screw engagement (engagement) with the male screw 312 of the puncture needle 31.

At the time of connecting the puncture needle 31 and the connector 4, first, a needle tip section of the puncture needle 31 is inserted into the rotating tube 40 of the connector 4, and the puncture needle 31 and the connector 4 are positioned with respect to the direction of rotation about the axis. Then, the rotating tube 40 is rotated in a direction for fastening (tightening the screw engagement). By this, the rotating tube 40 is fastened, whereby the puncture needle 31 and the connector 4 are connected and the connected state is fixed. For example, the puncture needle 31 and the connector 4 are connected, and the puncture needle 31 and the connector 4 are mutually fixed so that they will not relatively rotate about the axis or relatively move in the axial direction.

According to this puncture needle assembly 1, the same or equivalent effects to those of the aforementioned first embodiment can be obtained.

Note that in the present disclosure, a configuration may be adopted in which a male screw is formed on the connector 4 side and a female screw is formed on the puncture needle 31 side.

While a puncture needle assembly according to the described mode of the present disclosure has been described above with reference to the embodiments illustrated in the drawings, the present disclosure is not limited to the embodiments. The configuration of each component may be replaced by an arbitrary one having a function equivalent to the original. Besides, an arbitrary structure or structures may be added to the configuration according to the present disclosure.

In the present disclosure, there may be adopted a combination of arbitrary two or more configurations (features) of the aforementioned embodiment.

In the present disclosure, the shaft section and the connection section of the puncture member may be omitted.

While the puncture needle is, in its entirety, curved in a circular arc shape in the above embodiments, this is not restrictive in the present disclosure. For example, the puncture needle may be curved in a circular arc shape in only part thereof. The shape of the curved part of the puncture needle is not limited to the circular arc shape. Further, the puncture needle may be, for example, straight in shape.

While the sheath (retaining member) is, in its entirety, curved in a circular arc shape in the above embodiments, this is not restrictive in the present disclosure. For instance, the sheath may be curved in a circular arc shape in only part thereof. The shape of the curved part of the sheath is not restricted to the circular arc shape. Further, the sheath may be, for example, straight in shape.

While the connector and the sheath are composed of separate members in the above embodiments, this is not restrictive in the present disclosure. For example, the connector and the sheath may be formed to be integral with each other.

While the case where the puncture needle assembly according to the described mode of the present disclosure is applied to a medical device for use in embedding in a living body an embeddable implant for treatment of female urinary incontinence has been described in the above embodiment, this is not restrictive of the use of the puncture needle assembly of the present disclosure.

For example the target of the application of the present disclosure includes excretory disorders attendant on the weakening of the pelvic floor muscle group (urinary urgency, frequent urination, urinary incontinence, fecal incontinence, urinary retention, dysuria or the like), and pelvic floor disorders including pelvic organ prolapse, vesicovaginal fistula, urethrovaginal fistula, pelvic pain or the like. In the pelvic organ prolapse, there are included disorders of cystocele, enterocele, rectocele, hysterocele and the like. Alternatively, there are included such disorders as anterior vaginal prolapse, posterior vaginal prolapse, vaginal stump prolapse, vaginal vault prolapse and the like in which the naming method thereof is based on the prolapsed vaginal-wall part.

Also, overactive tissues include bladder, vagina, uterus, bowel and the like. Lessactive tissues include bones, muscles, fascias, ligaments and the like. In particular, in the case of pelvic floor disorders, the lessactive tissues include an obturator fascia, a coccygeus fascia, a cardinal ligament, an uterosacral ligament, a sacrospinous ligament and the like.

For the procedure for interlocking an overactive tissue in the pelvic floor disorder with the lessactive tissue, there are included a retropubic sling surgery, a transobturator sling surgery (transobturator tape (TOT) surgery), a tension-free vaginal mesh (TVM) surgery, a uterosacral ligament suspension (USLS) surgery, a sacrospinous ligament fixation (SSLF) surgery, an iliococcygeus fascia fixation surgery, a coccygeus fascia fixation surgery, and the like.

A puncture needle assembly of the present disclosure can include a puncture needle adapted to puncture biological tissue and a connector adapted to connect an elongated body insertable in a living body to a needle tip section of the puncture needle, the connector having a dissecting section adapted to dissect biological tissue by moving in a direction opposite to a direction in which the puncture needle punctures the biological tissue, wherein the puncture needle assembly further includes a connection mechanism capable of connecting the puncture needle and the connector to each other and a rotation restricting mechanism adapted to restrict rotation about an axis of the connector in relation to the puncture needle.

According to this disclosure, at the time of inserting an elongated body in a predetermined orientation into a patient's body, the inserting operation can be carried out relatively easily and reliably. In addition, the burden on the patient can be relatively low, and the safety of the patient can be relatively high. Further, the safety of the operator can also be relatively high.

For instance, where the puncture needle assembly of the present disclosure is used for treatment of female urinary incontinence, the elongated implant for treatment of urinary incontinence can be embedded without need to incise the vaginal wall. Thus, the implant can be embedded by a relatively low invasive procedure. Further, such a situation that, as in a case in which the vagina is incised, the implant is exposed to the inside of the vagina through the wound caused by the incision or that such complications as an infection from the wound occur can be prevented. Therefore, the implant can be embedded in very high safety and with certainty.

In addition, it is possible, for example, to dissect biological tissue in a predetermined width by the dissecting section. Accordingly, the implant can be embedded reliably by a very low invasive procedure.

Accordingly, the puncture needle assembly of the present disclosure has industrial applicability.

The detailed description above describes a puncture needle assembly. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A puncture needle assembly, the puncture needle assembly comprising:
   a puncture needle adapted to puncture biological tissue;
   a connector adapted to connect an elongated body insertable in a living body to a needle tip section of the puncture needle, the connector having a dissecting section adapted to dissect the biological tissue by moving in a direction opposite to a direction in which the puncture needle punctures the biological tissue, the connector having a main body having a cross-sectional shape, the cross-sectional shape of the main body having a width in one direction and a thickness in an other direction, the other direction being perpendicular to the one direction, and wherein the width of the main body of the connector is greater than the thickness of the main body of the connector, the thickness being measured from one outer surface of the connector to an other outer surface of the connector;
   a connection mechanism capable of connecting the puncture needle and the connector to each other; and
   a rotation restricting mechanism adapted to restrict rotation about an axis of the connector in relation to the puncture needle.

2. The puncture needle assembly according to claim 1, wherein the connection mechanism is provided in the puncture needle and the connector, and is configured to connect the puncture needle and the connector in such a manner that a positional relation of the puncture needle and the connector in a direction of rotation about the axis is constant.

3. The puncture needle assembly according to claim 1, wherein the connection mechanism is configured to connect the puncture needle and the connector by relatively moving the puncture needle and the connector in an axial direction.

4. The puncture needle assembly according to claim 3, wherein the connection mechanism includes a first connection section provided in the puncture needle, and a second connection section provided in the connector;
   the first connection section having a first recess in the needle tip section of the puncture needle; and
   the second connection section having a connector-side engaging section which engages with the first recess in a connected state.

5. The puncture needle assembly according to claim 4, wherein the connector-side engaging section has a connector-side projection which projects toward a proximal side in the axial direction.

6. The puncture needle assembly according to claim 4, wherein one of the first connection section and the second connection section has a second recess; and
   the other of the first connection section and the second connection section has a projection which engages with the second recess in the connected state.

7. The puncture needle assembly according to claim 4, further comprising:
   an inside of the first recess extending to a more distal side than an entrance to the first recess; and
   the inside of the first recess extending to a more proximal side than the entrance to the first recess.

8. The puncture needle assembly according to claim 4, wherein the connector on a distal side of the connector-side engaging section of the connector has a hole into which the needle tip section of the puncture needle is inserted at a time of connecting the puncture needle and the connector.

9. The puncture needle assembly according to claim 4, wherein the second connection section has a tubular section into which the needle tip section of the puncture needle is inserted; and
   the needle tip section of the puncture needle is inserted into the tubular section at a time of connecting the puncture needle and the connector.

10. The puncture needle assembly according to claim 9, wherein the connector-side engaging section has a connector-side projecting piece which is elastic and projects toward a distal side in the axial direction.

11. The puncture needle assembly according to claim 1, wherein the connection mechanism is configured to connect the puncture needle and the connector by relatively rotating at least part of the puncture needle and at least part of the connector.

12. The puncture needle assembly according to claim 1, wherein the rotation restricting mechanism includes a first rotation restricting section provided in the puncture needle, and a second rotation restricting section provided in the connector;
    the first rotation restricting section having a first recess in a needle tip section of the puncture needle; and
    the second rotation restricting section having a contact surface configured to make contact with an inner surface of the first recess in a connected state.

13. The puncture needle assembly according to claim 1, wherein the rotation restricting mechanism includes a first rotation restricting section provided in the puncture needle, and a second rotation restricting section provided in the connector;

the first rotation restricting section having a puncture needle-side projecting piece which is elastic and projects toward a proximal side in an axial direction; and the second rotation restricting section having a connector-side projecting piece which is elastic, projects toward a distal side in an axial direction and configured to make contact with the puncture needle-side projecting piece in a connected state.

14. The puncture needle assembly according to claim 1, comprising a connection release preventing mechanism adapted to prevent a connected state from being released.

15. The puncture needle assembly according to claim 1, wherein the width of the connector coincides with a width of the elongated body.

16. A puncture needle assembly, the puncture needle assembly comprising:

a puncture needle adapted to puncture biological tissue;

a connector adapted to connect an elongated body insertable in a living body to a needle tip section of the puncture needle, the connector having a dissecting section adapted to dissect biological tissue by moving in a direction opposite to a direction in which the puncture needle punctures the biological tissue, the connector having a main body having a cross-sectional shape, the cross-sectional shape of the main body having a width in one direction and a thickness in an other direction, the other direction being perpendicular to the one direction, and wherein the width of the main body of the connector is greater than the thickness of the main body of the connector, the thickness being measured from one outer surface of the connector to an other outer surface of the connector; and a connection mechanism capable of connecting the puncture needle and the connector to each other.

17. The puncture needle assembly according to claim 16, wherein the connection mechanism is provided in the puncture needle and the connector, and is configured to connect the puncture needle and the connector in such a manner that a positional relation of the puncture needle and the connector in a direction of rotation about the axis is constant.

18. The puncture needle assembly according to claim 16, wherein the connection mechanism is configured to connect the puncture needle and the connector by relatively moving the puncture needle and the connector in an axial direction.

19. The puncture needle assembly according to claim 18, wherein the connection mechanism includes a first connection section provided in the puncture needle, and a second connection section provided in the connector;

the first connection section has a first recess in the needle tip section of the puncture needle; and the second connection section has a connector-side engaging section which engages with the first recess in a connected state.

20. A method of inserting an elongated body in a living body, the method comprising:

puncturing biological tissue with a puncture needle;

connecting the elongated body to a needle tip section of the puncture needle;

connecting a connector to the puncture needle, the connector having a dissecting section adapted to dissect the biological tissue by moving in a direction opposite to a direction in which the puncture needle punctures the biological tissue, the connector having a main body having a cross-sectional shape, the cross-sectional shape of the main body having a width in one direction and a thickness in an other direction, the other direction being perpendicular to the one direction, and wherein the width of the main body of the connector is greater than the thickness of the main body of the connector, the thickness being measured from one outer surface of the connector to an other outer surface of the connector; and moving the connector in the direction opposite to the direction in which the puncture needle punctures the biological tissue.

* * * * *